US011854540B2

(12) United States Patent
Maitra et al.

(10) Patent No.: US 11,854,540 B2
(45) Date of Patent: Dec. 26, 2023

(54) UTILIZING MACHINE LEARNING MODELS TO GENERATE AUTOMATED EMPATHETIC CONVERSATIONS

(71) Applicant: Accenture Global Solutions Limited, Dublin (IE)

(72) Inventors: Anutosh Maitra, Bangalore (IN); Shubhashis Sengupta, Bangalore (IN); Sowmya Rasipuram, Bangalore (IN); Roshni Ramesh Ramnani, Bangalore (IN); Junaid Hamid Bhat, Tral (IN); Sakshi Jain, Bangalore (IN); Manish Agnihotri, Gwalior (IN); Dinesh Babu Jayagopi, Bangalore (IN)

(73) Assignee: Accenture Global Solutions Limited, Dublin (IE)

( * ) Notice: Subject to any disclaimer, the term of this patent is extended or adjusted under 35 U.S.C. 154(b) by 344 days.

(21) Appl. No.: 17/301,489

(22) Filed: Apr. 5, 2021

(65) Prior Publication Data
US 2022/0230632 A1    Jul. 21, 2022

(30) Foreign Application Priority Data

Jan. 8, 2021  (IN) .............................. 202141000924

(51) Int. Cl.
*G10L 15/183*     (2013.01)
*G10L 15/18*      (2013.01)
(Continued)

(52) U.S. Cl.
CPC ........ *G10L 15/1815* (2013.01); *A61B 5/0077* (2013.01); *A61B 5/1107* (2013.01);
(Continued)

(58) Field of Classification Search
CPC . G06T 7/70; G06T 2207/10016; G06V 20/41; G06V 40/168; G06V 40/16; G06N 20/20; G06N 20/10; G06F 18/24133
See application file for complete search history.

(56) References Cited

U.S. PATENT DOCUMENTS 11,545,173 B2 *   1/2023   Provost .................. G06N 20/00
11,645,479 B1 *   5/2023   Coursey ................. G06F 40/58
                                                                 704/9

(Continued)

FOREIGN PATENT DOCUMENTS

CA          3099832 A1      11/2019

OTHER PUBLICATIONS

Yang et al. "Hybrid Depression Classification and Estimation from Audio Video and Text Information". AVEC'17, Oct. 23, 2017, Mountain View, CA, USA (Year: 2017).*

(Continued)

*Primary Examiner* — Jesse S Pullias
(74) *Attorney, Agent, or Firm* — Harrity & Harrity, LLP

(57) ABSTRACT

A device may receive text data, audio data, and video data associated with a user, and may process the received data, with a first model, to determine a stress level of the user. The device may process the received data, with second models, to determine depression levels of the user, and may combine the depression levels to identify an overall depression level. The device may process the received data, with a third model, to determine a continuous affect prediction, and may process the received data, with a fourth model, to determine an emotion of the user. The device may process the received data, with a fifth model, to determine a response to the user, and may utilize a sixth model to determine a context for the response. The device may utilize seventh models to generate (Continued)

contextual conversation data, and may perform actions based on the contextual conversational data.

20 Claims, 10 Drawing Sheets

(51) Int. Cl.
G06T 7/70 (2017.01)
G10L 25/63 (2013.01)
G06F 40/35 (2020.01)
G10L 25/57 (2013.01)
G10L 15/16 (2006.01)
G10L 15/22 (2006.01)
G10L 25/90 (2013.01)
G06N 3/08 (2023.01)
G06N 3/04 (2023.01)
A61B 5/16 (2006.01)
A61B 5/00 (2006.01)
A61B 5/11 (2006.01)
G06V 20/40 (2022.01)
G06V 40/16 (2022.01)
G06N 3/0455 (2023.01)

(52) U.S. Cl.
CPC ........... *A61B 5/1114* (2013.01); *A61B 5/1128* (2013.01); *A61B 5/163* (2017.08); *A61B 5/165* (2013.01); *A61B 5/4803* (2013.01); *A61B 5/7267* (2013.01); *G06F 40/35* (2020.01); *G06N 3/04* (2013.01); *G06N 3/0455* (2023.01); *G06N 3/08* (2013.01); *G06T 7/70* (2017.01); *G06V 20/41* (2022.01); *G06V 40/168* (2022.01); *G10L 15/16* (2013.01); *G10L 15/183* (2013.01); *G10L 15/22* (2013.01); *G10L 25/57* (2013.01); *G10L 25/63* (2013.01); *G10L 25/90* (2013.01); *G06T 2207/10016* (2013.01); *G06T 2207/20081* (2013.01); *G06T 2207/20084* (2013.01); *G06T 2207/30201* (2013.01); *G10L 2015/223* (2013.01)

(56) References Cited

U.S. PATENT DOCUMENTS

2019/0385711 A1 12/2019 Shriberg et al.
2020/0075040 A1 3/2020 Provost et al.
2021/0192140 A1* 6/2021 Galley .................... G06F 40/35
2021/0319897 A1* 10/2021 Howard ................. G16H 40/67

OTHER PUBLICATIONS

Ouerhani et al. "Smart Ubiquitous Chatbot for COVID-19 Assitance with Deep Learning Sentiment Analysis Model During and After Quarantine" (2020), 10.21203/rs.3.rs-33343/v1 (Year: 2020).*
Pampouchidou et al. "Depression Assessment by Fusing High and Low Level Features from Audio, Video, and Text". AVEC'16, Oct. 16, 2016, Amsterdam, Netherlands (Year: 2016).*
Rasipuram et al., "Multi-modal Sequence-to-sequence Model for Continuous Affect Prediction in the Wild Using Deep 3D Features," 2020 15th IEEE International Conference on Automatic Face and Gesture Recognition (FG 2020), Nov. 16-20, 2020, 4 Pages.
Rasipuram et al., "Multi-modal Expression Recognition in the Wild Using Sequence Modeling," 2020 15th IEEE International Conference on Automatic Face and Gesture Recognition (FG 2020), Nov. 16-20, 2020, 3 Pages.
Agnihotri et al., "Towards Generating Affective and Topic-driven Responses," ICPR International Workshops and Challenges, ICPR 2021, Published Online Feb. 23, 2021, 14 Pages.

* cited by examiner

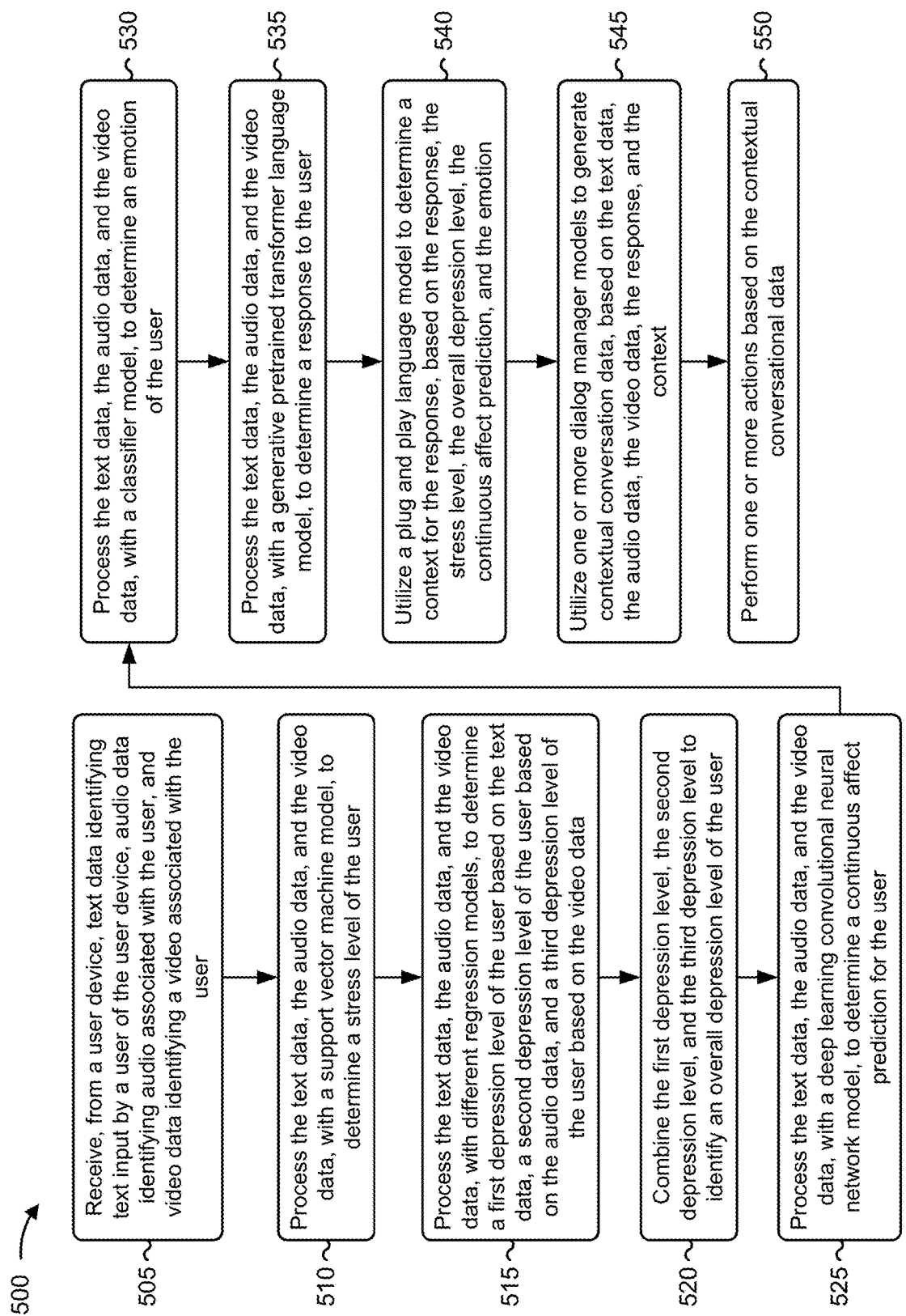

UTILIZING MACHINE LEARNING MODELS TO GENERATE AUTOMATED EMPATHETIC CONVERSATIONS

CROSS-REFERENCE TO RELATED APPLICATION

This application claims priority to Indian Provisional Application No. 202141000924 entitled "UTILIZING MACHINE LEARNING MODELS TO GENERATE AUTOMATED EMPATHETIC CONVERSATIONS," filed on Jan. 21, 2021. The entire content of which is expressly incorporated herein by reference.

BACKGROUND

A virtual conversational agent is a software application used to conduct an on-line conversation via text or speech, in lieu of providing direct contact with a live human agent. Designed to convincingly simulate the way a human would behave as a conversational partner, conversational agents typically require continuous training on human behavioral traits, tuning to different kinds of business applications and testing, and many in production remain unable to adequately converse.

SUMMARY

In some implementations, a method may include receiving, from a user device, text data identifying text input by a user of the user device, audio data identifying audio associated with the user, and video data identifying a video associated with the user, and processing the text data, the audio data, and the video data, with a support vector machine model, to determine a stress level of the user. The method may include processing the text data, the audio data, and the video data, with different regression models, to determine a first depression level of the user based on the text data, a second depression level of the user based on the audio data, and a third depression level of the user based on the video data, and combining the first depression level, the second depression level, and the third depression level to identify an overall depression level of the user. The method may include processing the text data, the audio data, and the video data, with a deep learning convolutional neural network model, to determine a continuous affect prediction for the user, and processing the text data, the audio data, and the video data, with a classifier model, to determine an emotion of the user. The method may include processing the text data, the audio data, and the video data, with a generative pretrained transformer language model, to determine a response to the user, and utilizing a plug and play language model to determine a context for the response, based on the response, the stress level, the overall depression level, the continuous affect prediction, and the emotion. The method may include utilizing one or more dialog manager models to generate contextual conversation data, based on the text data, the audio data, the video data, the response, and the context, and performing one or more actions based on the contextual conversational data.

In some implementations, a device includes one or more memories and one or more processors to receive, from a user device, text data identifying text input by a user of the user device, audio data identifying audio associated with the user, and video data identifying a video associated with the user, and process the text data, the audio data, and the video data, with a support vector machine model, to determine a stress level of the user. The one or more processors may process the text data, the audio data, and the video data, with different regression models, to determine a first depression level of the user based on the text data, a second depression level of the user based on the audio data, and a third depression level of the user based on the video data, and may assign weights to the first depression level, the second depression level, and the third depression level to generate a first weighted depression level, a second weighted depression level, and a third weighted depression level. The one or more processors may aggregate the first weighted depression level, the second weighted depression level, and the third weighted depression level to identify an overall depression level of the user, and may process the text data, the audio data, and the video data, with a deep learning convolutional neural network model, to determine a continuous affect prediction for the user. The one or more processors may process the text data, the audio data, and the video data, with a classifier model, to determine an emotion of the user, and may process the text data, the audio data, and the video data, with a generative pretrained transformer language model, to determine a response to the user. The one or more processors may utilize a plug and play language model to determine a context for the response, based on the response, the stress level, the overall depression level, the continuous affect prediction, and the emotion, and may utilize one or more dialog manager models to generate contextual conversation data, based on the text data, the audio data, the video data, the response, and the context. The one or more processors may perform one or more actions based on the contextual conversational data.

In some implementations, a non-transitory computer-readable medium may store a set of instructions that includes one or more instructions that, when executed by one or more processors of a device, cause the device to receive, from a user device, text data identifying text input by a user of the user device, audio data identifying audio associated with the user, and video data identifying a video associated with the user, and process the text data, the audio data, and the video data, with a support vector machine model, to determine a stress level of the user. The one or more instructions may cause the device to process the text data, the audio data, and the video data, with different regression models, to determine a first depression level of the user based on the text data, a second depression level of the user based on the audio data, and a third depression level of the user based on the video data, and combine the first depression level, the second depression level, and the third depression level to identify an overall depression level of the user. The one or more instructions may cause the device to process the text data, the audio data, and the video data, with a deep learning convolutional neural network model, to determine a continuous affect prediction for the user, wherein the continuous affect prediction for the user includes an arousal prediction for the user and a valence prediction for the user. The one or more instructions may cause the device to process the text data, the audio data, and the video data, with a classifier model, to determine an emotion of the user, and process the text data, the audio data, and the video data, with a generative pretrained transformer language model, to determine a response to the user. The one or more instructions may cause the device to utilize a plug and play language model to determine a context for the response, based on the response, the stress level, the overall depression level, the continuous affect prediction, and the emotion, and utilize one or more dialog manager models to generate contextual conversation data, based on the text data, the audio data, the video data, the response, and the context. The one or more instructions may cause the device to perform one or more actions based on the contextual conversational data.

BRIEF DESCRIPTION OF THE DRAWINGS

FIG. 5 is a flowchart of an example process for utilizing machine learning models to generate automated empathetic conversations.

DETAILED DESCRIPTION

Figure 1A:
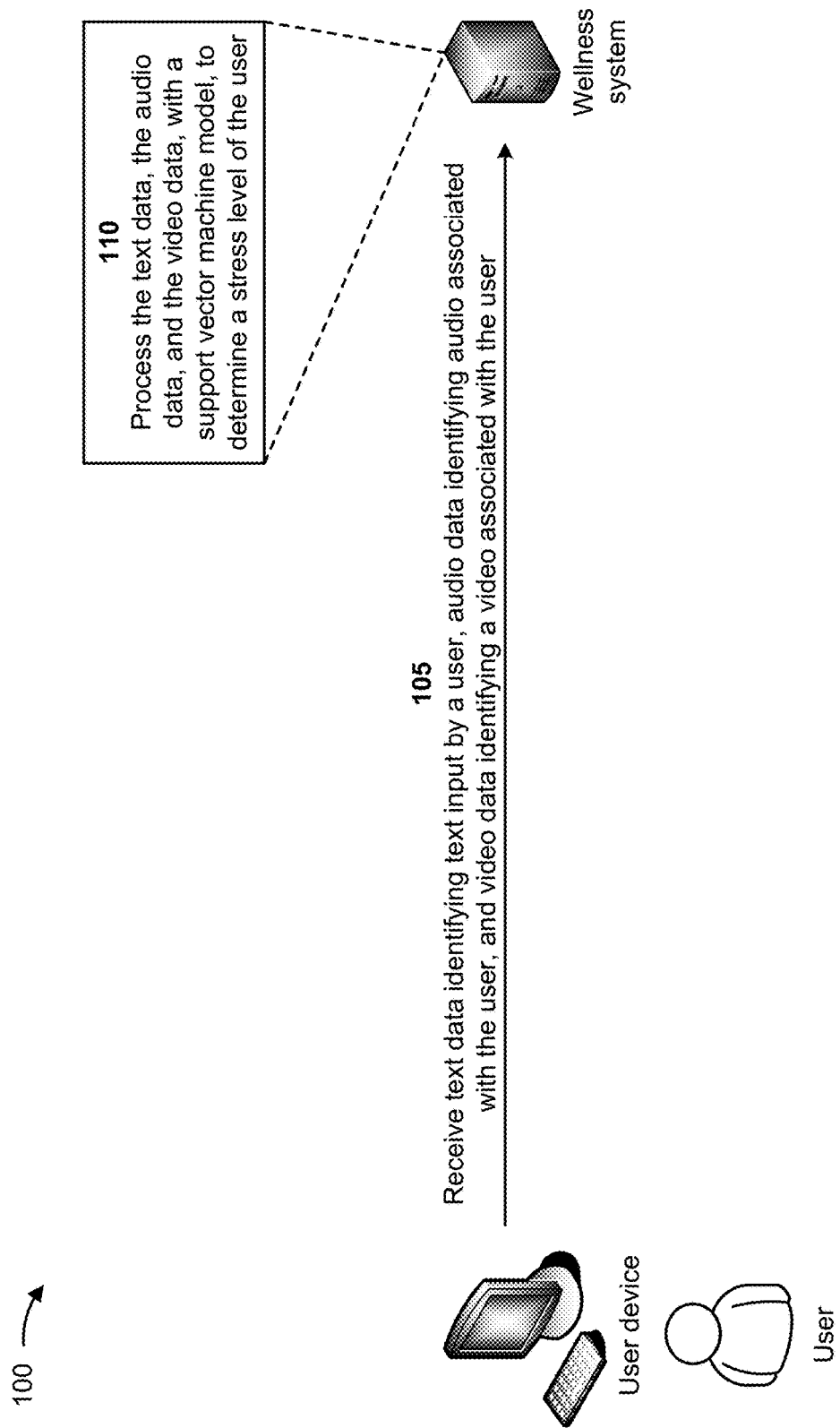
FIGS. 1A-1F are diagrams of an example implementation described herein.

The following detailed description of example implementations refers to the accompanying drawings. The same reference numbers in different drawings may identify the same or similar elements.

Current conversational agents are unable to recognize stress, depression, and/or other disorders associated with users interacting with the conversational agents. This is because conversational agents are unable to identify stress levels, depression levels, and emotions of people. Thus, conversational agents are unable to automatically generate empathetic conversations tailored to people's stress levels, depression levels, and emotions, and that enable treatment of the stress levels, depression levels, and emotions. The stress levels, depression levels, and emotions may cause people to miss work, may decrease productivity of the people, may cause people to quit jobs, and/or the like. Therefore, current conversational agents waste computing resources (e.g., processing resources, memory resources, communication resources, and/or the like), networking resources, human resources, and/or the like associated with reduced work productivity, missed workdays, handling disability claims, injuries, handling grievances, handling turnover, and/or the like.

Some implementations described herein relate to a wellness system that utilizes machine learning models to generate automated empathetic conversations. For example, the wellness system may receive, from a user device, text data identifying text input by a user of the user device, audio data identifying audio associated with the user, and video data identifying a video associated with the user, and may process the text data, the audio data, and the video data, with a support vector machine model, to determine a stress level of the user. The wellness system may process the text data, the audio data, and the video data, with different regression models, to determine a first depression level of the user based on the text data, a second depression level of the user based on the audio data, and a third depression level of the user based on the video data, and may combine the first depression level, the second depression level, and the third depression level to identify an overall depression level of the user. The wellness system may process the text data, the audio data, and the video data, with a deep learning convolutional neural network model, to determine a continuous affect prediction for the user, and may process the text data, the audio data, and the video data, with a classifier model, to determine an emotion of the user. The wellness system may process the text data, the audio data, and the video data, with a generative pretrained transformer language model, to determine a response to the user, and may utilize a plug and play language model to determine a context for the response, based on the response, the stress level, the overall depression level, the continuous affect prediction, and the emotion. The wellness system may utilize one or more dialog manager models to generate contextual conversation data, based on the text data, the audio data, the video data, the response, and the context, and may perform one or more actions based on the contextual conversational data.

In this way, the wellness system utilizes machine learning models to generate automated empathetic conversations. The wellness system may improve mental wellness in a workplace by providing empathetic advisement in a proactive, personalized, contextual, and guided manner. Employees and/or patients exposed to high stress in professional and/or personal environments may utilize the wellness system as an empathetic companion to which to talk via text, voice, and/or video. The wellness system may provide early monitoring and detection of degrees of stress and depression of users of the wellness system. The wellness system may suggest remedial measures to the users, may guide conversations to soothe the users, and may suggest appropriate counselors for the users. The wellness system provides personalized conversations, trustworthy interactions, mood-aware interactions, context-aware conversations, and/or the like. This, in turn, conserves computing resources, networking resources, human resources, and/or the like that would otherwise have been wasted in reduced work productivity, missed workdays, handling disability claims, injuries, handling grievances, handling turnover, and/or the like.

In contrast, chatbots are rarely required to understand stress or emotion during execution because chatbots follow a technology of dialog flow through a dialog manager, which often identifies text content (e.g., from typed words or by a text-to-speech model) and positive or negative sentiment from the text content, and guides the dialog flow in a pre-scripted manner. Whereas, the wellness system provides a conversational agent that interacts with a user through natural speech that cannot be pre-scripted and through a conversation that adapts to content presented on the fly while keeping the conversation within context. The conversational agent may even change a discourse of the conversation if the user changes the dialog to another context (or intent) on the fly. The conversational agent may understand not only the content of the conversation, but may also recognize a manner in which the content is presented and may respond accordingly to eliminate a possibility of a conversational fallout.

For example, if a user says or types "Please arrange for the refund, I am not happy with this product," or the user says or types "Why do you sale such rubbish? Take back this piece of filth, can I get my money back," the conversational agent may identify such content as "Please arrange for the refund, I am not happy with this product." However, a response of the conversational agent (e.g., which is fully unscripted and machine-trained based on large quantity of past scenarios where human agents converse in real cases) may or may not be the same in these two cases and may depend on voice tonality, facial expression, body gesture, posture, and/or the like of the user.

In some implementations, the wellness system may be utilized to identify an affect in general on the user. An affect may include pain, haste, an engagement level, despair, longing, fondness, and/or the like. In such implementations, the wellness system may remain unaltered, but the models described herein may need different sets of training data to be applicable to a corresponding end application.

FIGS. 1A-1F are diagrams of an example 100 associated with utilizing machine learning models to generate automated empathetic conversations. As shown in FIGS. 1A-1F, example 100 includes a user device associated with a user and a wellness system. The user device may include a laptop computer, a mobile telephone, a desktop computer, and/or the like associated with a user. The wellness system may include a system that utilizes machine learning models to generate automated empathetic conversations for the user of the user device. Although implementations are described herein in connection with stress, distress, and depression, the wellness system may be utilized to detect and address other emotions, such as an anger level of a customer, a pain level of a patient, and/or the like.

As shown in FIG. 1A, and by reference number 105, the wellness system may receive, from the user device, text data identifying text input by the user to the user device, audio data identifying audio associated with the user, and video data identifying a video associated with the user. The text data may include text input by the user via an input component (e.g., a keyboard) to the user device, text that is spoken by the user and provided to the user device via another input component (e.g., a microphone or a camera with a microphone), and/or the like. In some implementations, the wellness system performs natural language processing on the text that is spoken by the user in order to convert voice data of the user to textual data. The audio data may include audio captured by the other input component (e.g., the microphone or the camera with the microphone) of the user device. For example, the audio data may include data identifying a prosody, an intonation, a rhythm, a pitch, an intensity, a loudness, an energy, jitter, and/or the like associated with a voice of the user, background noise associated with the user device, and/or the like. The video data may include video captured by the other input component (e.g., the camera) of the user device. For example, the video data may include video and/or images of the user, visual features of the user (e.g., a yaw, a pitch, and/or roll angles associated with the user's head, an eye gaze of the user, an intensity of a contraction of a facial muscle of the user, and/or the like), video and/or images of a background associated with the user, and/or the like.

As further shown in FIG. 1A, and by reference number 110, the wellness system may process the text data, the audio data, and the video data, with a support vector machine model, to determine a stress level of the user. The support vector machine may include a classifier model that is trained with an acted facial expressions in the wild (AFEW) emotion-labelled corpus that is converted to stress and non-stress classes. In some implementations, the wellness system utilizes the support vector machine to determine a first stress level of the user based on the text input by the user, as provided in the text data. In some implementations, the wellness system utilizes the support vector machine to determine a second stress level of the user based on an intonation of a voice of the user, a rhythm of the voice, a pitch of the voice, an intensity of the voice, a loudness of the voice, a jitter of the voice, and/or the like, as provided in the audio data. In some implementations, the wellness system utilizes the support vector machine to determine a third stress level of the user based on a head pose of the user, an eye gaze of the user, an intensity of a facial muscle contraction of the user, and/or the like, as provided in the video data. The wellness system may combine the first stress level, the second stress level, and the third stress level to determine an overall stress level of the user.

Figure 1B:
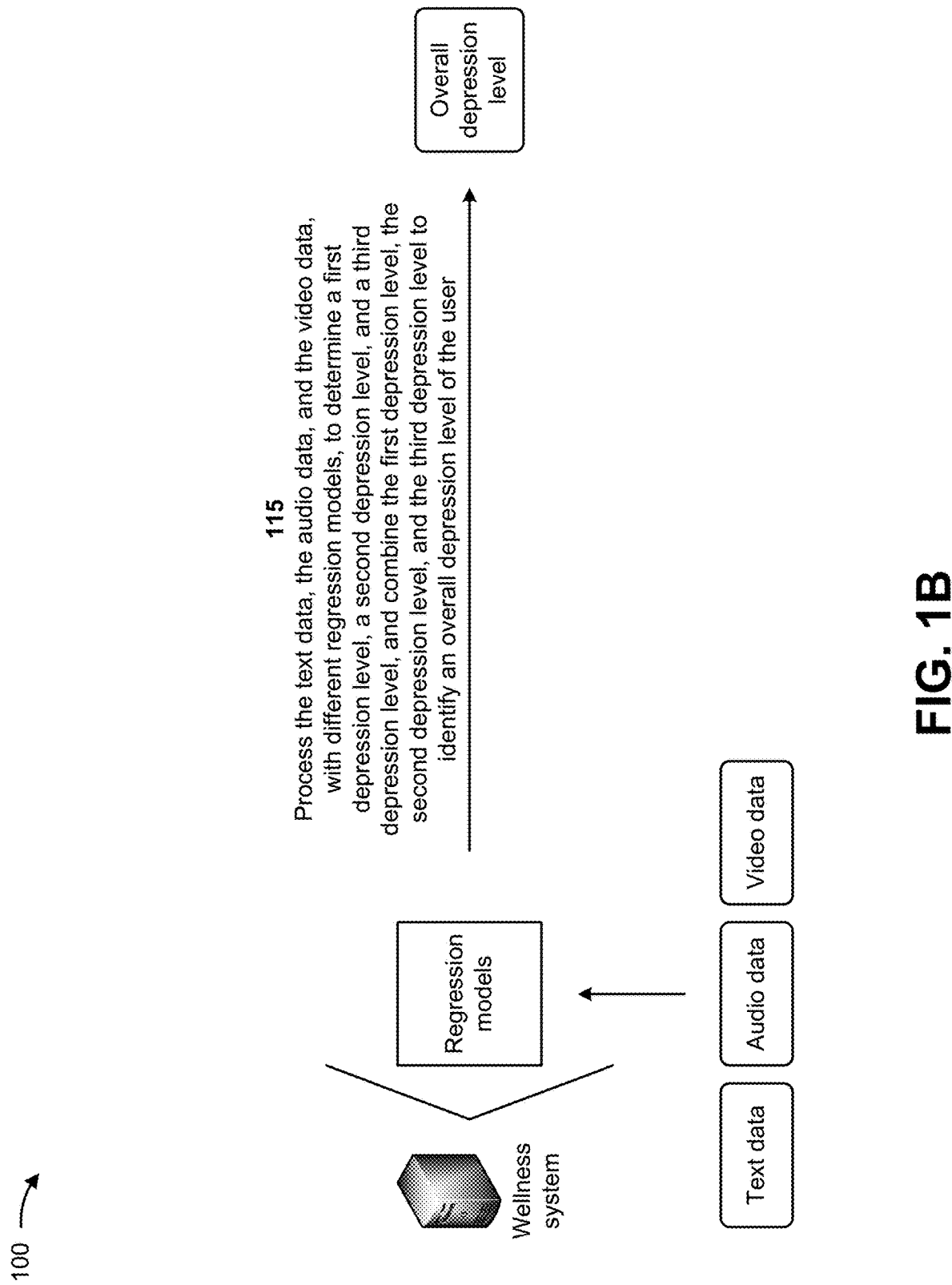

As shown in FIG. 1B, and by reference number 115, the wellness system may process the text data, the audio data, and the video data, with different regression models, to determine a first depression level, a second depression level, and a third depression level, and may combine the first depression level, the second depression level, and the third depression level to identify an overall depression level of the user. Depression is due to prolonged stress and may result in post-traumatic stress disorder (PTSD). Depression is a common mood disorder that is characterized by persistent negative affect. The different regression models may include different linear regression models. In some implementations, the different regression models include a first regression model to utilize with the text data, a second regression model to utilize with the audio data, and a third regression model to utilize with the video data. The wellness system may process the text data, with the first regression model, to determine the first depression level of the user, may process the audio data, with the second regression model, to determine the second depression level of the user, and may process the video data, with the third regression model, to determine the third depression level of the user.

The wellness system may aggregate the outputs of the different regression models (e.g., the first depression level, the second depression level, and the third depression level) in a weighted fashion that is based on mean absolute errors associated with the outputs of the different regression models. For example, the wellness system may assign, to the first depression level, a first weight (e.g., based on a mean absolute error of the first depression level) to generate a first weighted depression level. The wellness system may assign, to the second depression level, a second weight (e.g., based on a mean absolute error of the second depression level) to generate a second weighted depression level. The wellness system may assign, to the third depression level, a third weight (e.g., based on a mean absolute error of the third depression level) to generate a third weighted depression level. The wellness system may aggregate the first weighted depression level, the second weighted depression level, and the third weighted depression level to identify the overall depression level of the user. For example, the wellness system may add the first weighted depression level, the second weighted depression level, and the third weighted depression level to identify the overall depression level of the user. In another example, the wellness system may calculate an average of the first weighted depression level, the second weighted depression level, and the third weighted depression level to identify the overall depression level of the user.

Figure 1C:
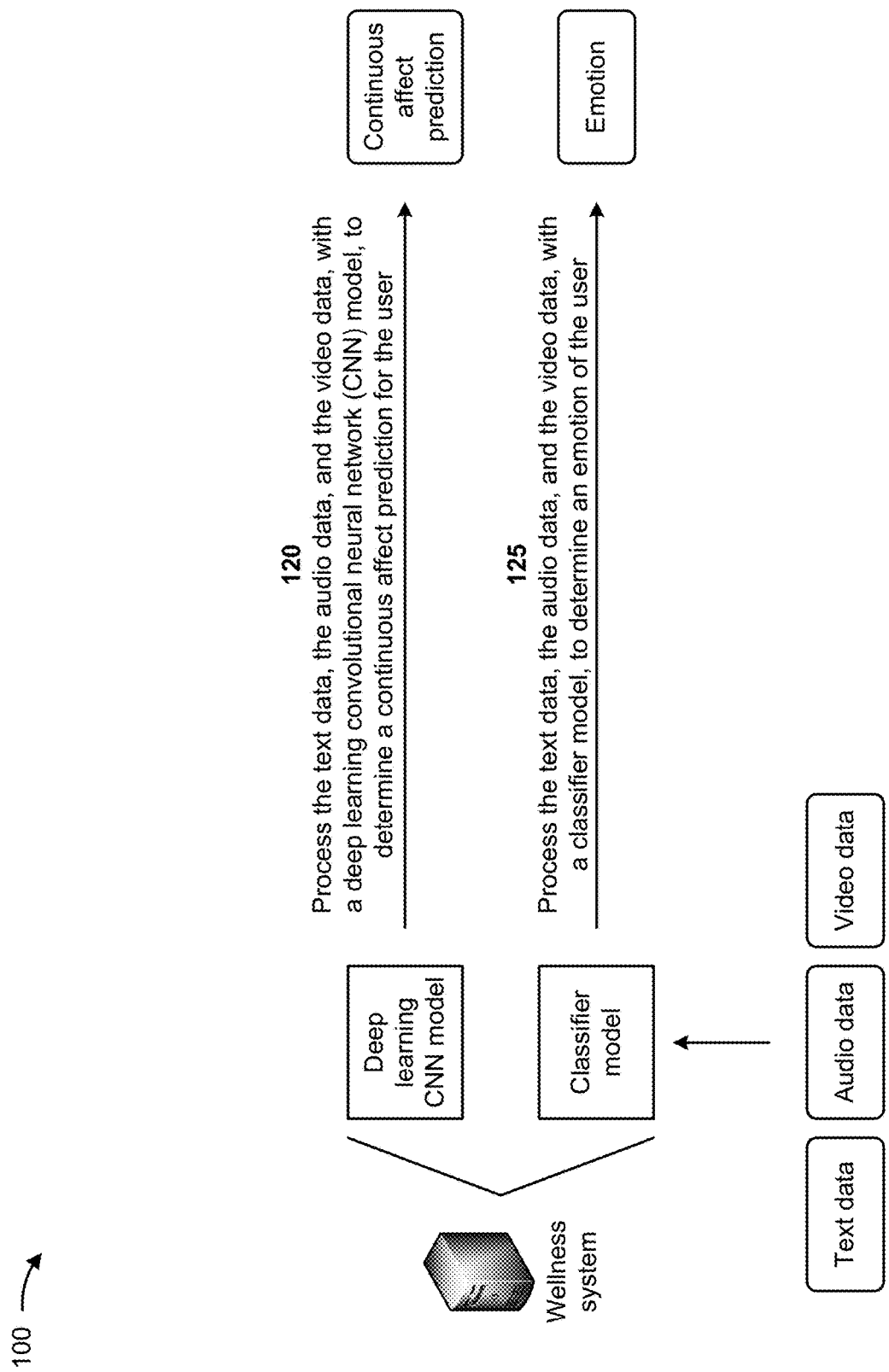

As shown in FIG. 1C, and by reference number 120, the wellness system may process the text data, the audio data, and the video data, with a deep learning convolutional neural network (CNN) model, to determine a continuous affect prediction for the user. The continuous affect prediction for the user may include an arousal prediction for the user and a valence prediction for the user. Emotional stimuli may be classified by considering two dimensions: valence, which describes an attractiveness (e.g., a positive valence) or an aversiveness (e.g., negative valence) of stimuli along a continuum (e.g., negative, neutral, or positive), and arousal, which refers to a perceived intensity of an event from very calming to highly exciting or agitating.

The deep learning CNN model may include a multi-modal sequence-to-sequence model. For example, the wellness system may utilize text data, audio data, and video data (e.g., multi-modal data) to train a sequence-to-sequence model that is based on gated recurrent units (GRUs). The multi-modal data may include videos that have left and right subjects and have been annotated for both separately. The multi-modal data may include videos that are distributed in all four quadrants of a valence and arousal space and may provide video samples with extreme human behavior in real world settings. The wellness system may split the multi-modal data into three parts for training, validation, and testing of the deep learning CNN model. The wellness system may pre-process the multi-modal data for face detection to extract cropped and aligned face images from all videos, may extract audio and visual features from the multi-modal data, and may training the deep learning CNN model using deep learning methods.

With respect to pre-processing the multi-modal data, the wellness system may utilize a face detector to extract aligned faces from the videos. The face detector may detect faces in robust environments when images are non-frontal, occluded, in low illumination conditions, and/or the like, and may output faces with a fixed dimension. The wellness system may utilize the faces for further visual feature extraction. The wellness system may extract audio signals from the videos and may utilize the audio signals for further audio feature extraction.

With respect to audio feature extraction, the wellness system may extract mel-frequency cepstral coefficients (MFCC) and mel-spectrogram coefficients. Such coefficients may be effective for emotion recognition tasks. The wellness system may split an audio signal into N overlapping segments, where N may correspond to a quantity of frames in a video. The overlap may be kept equal to a one-half split. The MFCCs may form a cepstral representation where frequency bands are not linear, but rather distributed according to the mel-scale. The mel-spectrogram (e.g., a mel-frequency spectrogram) may provide a signal strength at various frequencies. The wellness system may concatenate the audio features to form a feature vector and may combine frame-level audio features to form sequences for model training.

With respect to visual feature extraction, the wellness system may generate a visual representation for each aligned face. The wellness system may utilize a landmark free approach to generate three-dimensional expression coefficients based on CNN, which is a deep learning-based method that produces a three-dimensional morphable model (3DMM) representation of the input face. The wellness system may capture not only shapes of faces, but also may determine positions and emotions. For example, the wellness system may determine features, such as emotions, three-dimensional shapes of faces, positions of faces, and/or the like. The wellness system may extract features for all aligned face images and may combine a frame-level representation to form a sequence level representation. The sequence level features may be used for training the deep learning CNN model. The wellness system may also determine face pose features, such as a head pose, an eye gaze, action unit intensities, and/or the like. The wellness system may combine the face pose features to form sequence level features.

The wellness system may determine the audio features, visual features, and the face pose features separately before combining the features together. Combining the audio data and the video data prior to determining the audio features, the visual features, and the face pose features may generate a computationally expensive deep learning CNN model with a large quantity of parameters. In this way, the wellness system may conserve computing resources, networking resources, and/or the like that otherwise would have been wasted in executing a computationally expensive deep learning CNN model.

As further shown in FIG. 1C, and by reference number 125, the wellness system may process the text data, the audio data, and the video data, with a classifier model, to determine an emotion of the user. In some implementations, the classifier model includes a random forest classifier model, and the emotion of the user includes happiness, sadness, anger, surprise, neutral, contempt, fear, disgust, and/or the like. The wellness system may utilize a bi-modal approach by combining audio and visual features and training a sequence-to-sequence model that is based on GRUs and a long short-term memory (LSTM) network.

The wellness system may utilize the multi-modal data to train the classifier model. The wellness system may split the multi-modal data into three parts for training, validation, and testing of the classifier model. The wellness system may pre-process the multi-modal data for face detection to extract cropped and aligned face images from all videos, may extract audio and visual features from the multi-modal data, and may train the classifier model using deep learning methods. The wellness system may pre-process the multi-modal data, as described above, to extract faces and audio signals. The wellness system may utilize the faces for further visual feature extraction and may utilize the audio signals for further audio feature extraction.

The wellness system may extract the audio features and the visual features as described above. The wellness system may concatenate the audio features to form a feature vector and may combine frame-level audio features to form sequences for model training. With respect to visual feature extraction, the wellness system may determine face pose features, such as a head pose, an eye gaze, action unit intensities, and/or the like. The wellness system may combine the face pose features to form sequence level features.

The wellness system may determine the audio features and the face pose features separately before combining the features together. Combining the audio data and the video data prior to determining the audio features and the face pose features may generate a computationally expensive classifier model with a large quantity of parameters. In this way, the wellness system may conserve computing resources, networking resources, and/or the like that otherwise would have been wasted in executing a computationally expensive classifier model.

Figure 1D:
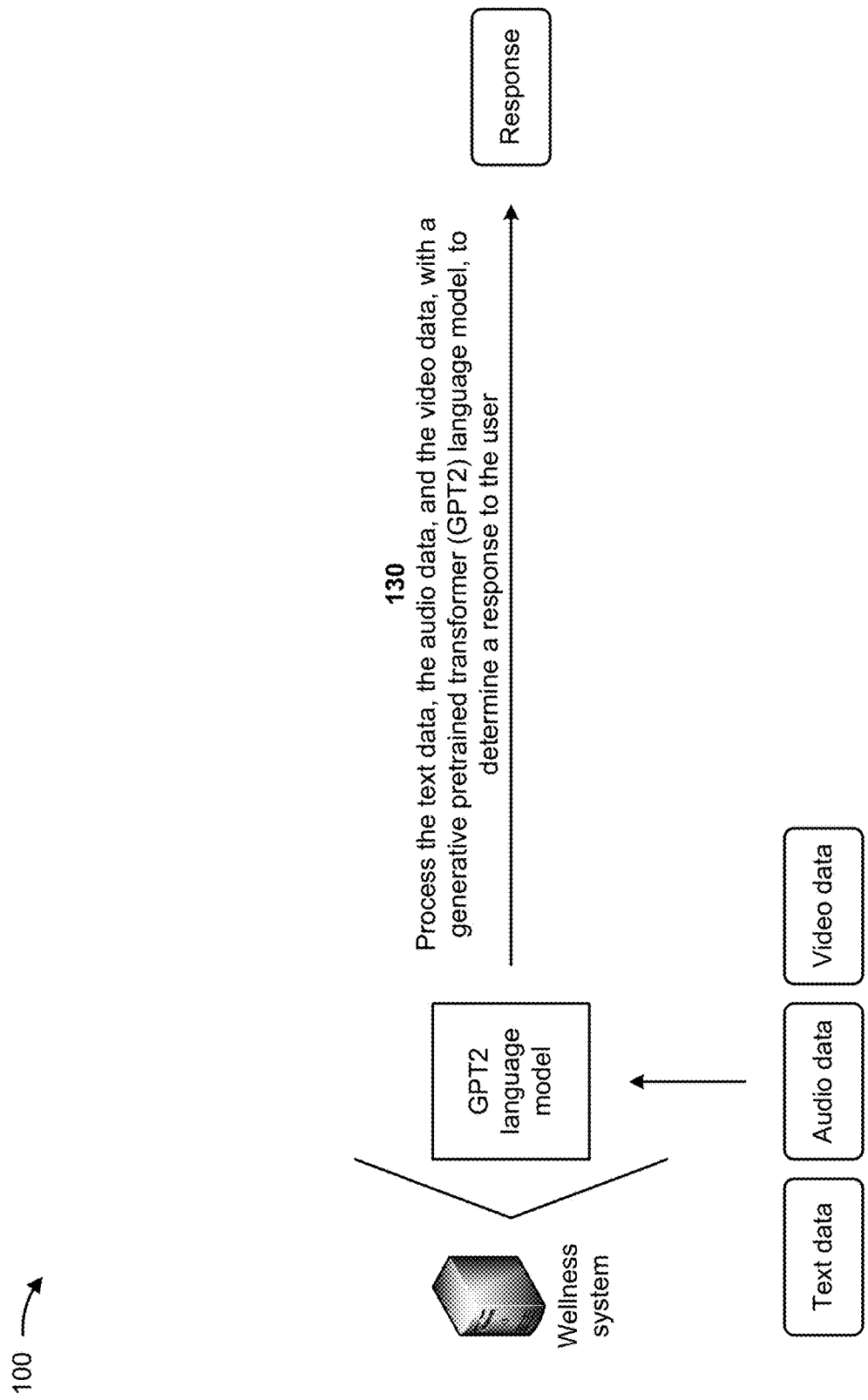

As shown in FIG. 1D, and by reference number 130, the wellness system may process the text data, the audio data, and the video data, with a generative pretrained transformer (GPT2) language model, to determine a response to the user. The response may include a domain specific contextual utterance that is unscripted. In some implementations, the GPT2 language model includes a sentiment portion that is trained based on an emotion class and by applying a cross-entropy loss to the sentiment portion. A dialog setting may include contexts, such as a history of the dialog (e.g., previous utterances) and tokens of an output sentence. The wellness system may generate input parallel sequences, such as positional embeddings, dialog state embeddings, and word embeddings, and may combine the input parallel sequences into a single sequence. The wellness system may utilize a multi-task loss that combines language modeling with a next-sentence prediction objective and that minimizes a total loss which is a weighted sum of a language modeling loss and a next-sentence prediction loss. With respect to the language modeling loss, the wellness system may project a hidden state on a word embedding matrix to obtain logits and may apply a cross-entropy loss on a portion of a target corresponding to a reply. With respect to a next-sentence prediction loss, the wellness system may pass a hidden state of a last token (e.g., an end-of-sequence token) through a linear layer to obtain a score and may apply a cross-entropy loss to correctly classify an answer among distractors. The wellness system may generate an empathetic response via a sentiment head by passing the hidden state of the last token through a linear layer, by applying a softmax model to the hidden state of the last token to obtain an emotion class, and by applying a cross-entropy loss to train the sentiment head to classify emotion correctly. The wellness system may further generate a more empathetic response by adding an emotion token in every sentence into the GPT2 language model and by causing the GPT2 language model to learn an association between the emotion token and relevant emotionally colored words.

The GPT2 language model may include a pre-trained language model that is trained on a vast corpus of text, enabling the GPT2 language model to generate a sequence of tokens resulting in a grammatically correct and coherent text. The wellness system may fine-tune the GPT2 language model to generate affective responses. The GPT2 language model may include a decoder component that utilizes multiple decoder layers, each containing two sub-layers. A first sub-layer includes a multi-headed self-attention mechanism over input context tokens, and a second sub-layer includes position-wise feed-forward layers to produce an output distribution over target tokens. In some implementations, the GPT2 language model may include a twenty-four-layer decoder with twenty-four self-attention heads containing multiple dimensional states. The wellness system may utilize a large-scale conversational dataset with utterance-level affective state labels to fine tune the GPT2 language model. The dataset may be annotated with positive, negative, and neutral labels. The dataset may include an utterance-level affective state and a conversation-level final affective state. The dataset may be well-proportioned on affective state information for both single utterance and single turn.

The GPT2 language model may utilize a multi-task loss combining a language modeling loss, a next-sentence prediction loss, and an affective state prediction loss. The next sentence prediction loss enables the GPT2 language model to learn to determine an appropriate response. The affective state prediction loss optimizes the GPT2 language model to predict a correct emotion for an utterance and to generate emotion-specific word tokens. A total loss for the GPT2 language model may include a weighted sum of the three losses. The wellness system may calculate the language modeling loss by projecting a hidden state of a last layer onto an embedding matrix to compute logits and by applying a cross-entropy loss on a generated response. The wellness system may calculate the next sentence prediction loss by inputting a hidden state of a last token through a linear layer and by computing a score to classify an actual answer among distractors correctly. The wellness system may calculate the affective state prediction loss by inputting a hidden state of a last token through another linear layer and by computing a score to classify an actual affective state among positive, negative, and neutral states.

The wellness system may fine tune the GPT2 language model with the dataset described above. The GPT2 language model may be fine-tuned for five epochs, for example, and a maximum quantity of previous exchanges to keep in history may be limited to six, for example. For a next sentence prediction loss, a classification head may classify a last token among ten options, which include a reply and nine distractors. The distractors may be uniform and randomly sampled from other conversations in the dataset to act as the distractors per each reply utterance. The wellness system may utilize a top-p nucleus sampling strategy for decoding. At each timestep, a probability of each word in a vocabulary being a next likely word is computed. The decoder may randomly sample a word from tokens with a cumulative probability just above a threshold value.

Figure 1E:
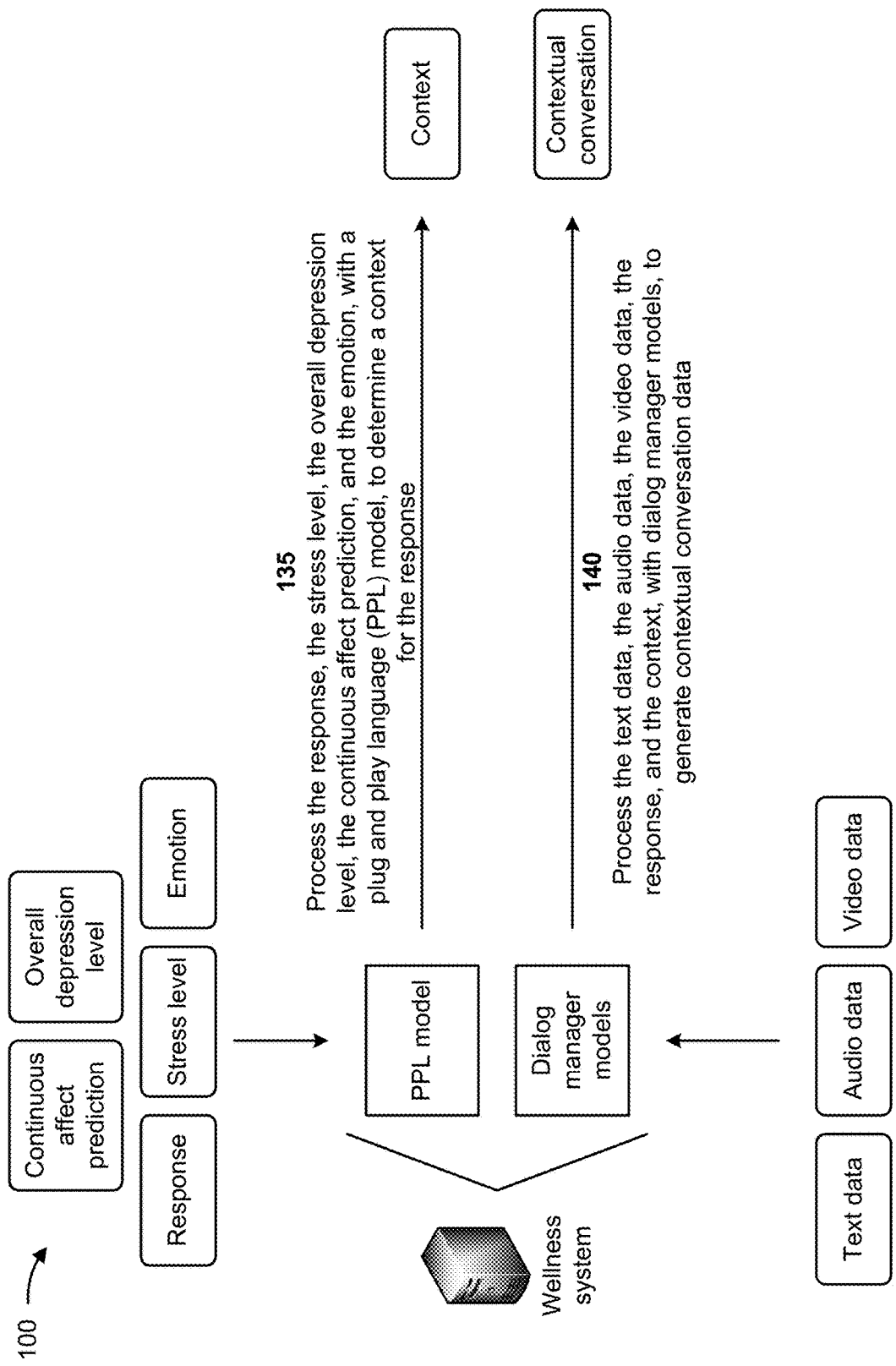

As shown in FIG. 1E, and by reference number 135, the wellness system may process the response, the stress level, the overall depression level, the continuous affect prediction, and the emotion, with a plug and play language (PPL) model, to determine a context for the response. In some implementations, the plug and play language model includes a language model and an attribute model. The wellness system may process the response, the stress level, the overall depression level, the continuous affect prediction, and the emotion, with the attribute model, to determine attributes and gradients, and may perform a forward pass with the language model to compute a likelihood of the attribute. The wellness system may perform a backward pass with the language model to update internal latent representations of the attribute based on the gradients and may determine the context for the response based on the updated internal latent representations of the attribute.

The PPL model may provide for controlled language generation and may combine a pretrained language model with classification models to steer text generation towards a list of specific topics. The PPL model may be much smaller than the language models described above and may not require fine tuning. In the PPL model, at every token generation step, a hidden state is shifted in a direction of a sum of two gradients (e.g., a first gradient towards a higher log-likelihood of a topic under a topic classifier, and second gradient toward higher log-likelihood of the language model of the PPL model). While the first gradient drives a presence of the topic, the second gradient ensures that language fluency is maintained. Following this update, the PPL model may generate a new distribution over the vocabulary and may sample a new token. Such a process may be performed multiple times for every token, resulting in a response with a greater relevance to the topic. The PPL model may also employ various steps that minimize degeneration of generated language.

The wellness system may identify and cluster the most common mental health problems and may select particular mental health problems on which people commonly converse (e.g., addiction, anxiety, disruption in daily activities, relationships, and self-harm). Addiction may include symptoms, such as smoking, drinking, speeding, or substance abuse. Anxiety may include symptoms related to feeling unusually confused, forgetful, angry, sad, or depressed. Disruption in daily activities may include symptoms of eating disorders, sleeping disorders, bipolar disorders, and existential crisis. Relationships may include symptoms of domestic violence, challenges in family dynamics and/or family members with personality disorders, and loss of a loved one. Self-harm may include symptoms of suicides, hearing voices, sadism, and narcissism. The wellness system may train a topic classifier model based on the selected mental health problems and may utilize the PPL model to generate a response that restricts a scope of a conversation to the selected mental health problems.

The wellness system may utilize a discriminator class as an attribute model in the PPL model to aid in generating responses that are empathetic and specific to a type of wellness issue under discussion. The discriminator is a classifier modeled as an approximator where vector embeddings of the conversation are compared with representative vector embeddings of each of the wellness classes and a class attribute is determined as a class with a representative vector closest to a vector representation of the new utterance.

As further shown in FIG. 1E, and by reference number 140, the wellness system may process the text data, the audio data, the video data, the response, and the context, with dialog manager models, to generate contextual conversation data. In some implementations, the dialog manager models include a support vector machine model, a logistic regression model, a random forest model, a conditional random field model, a bidirectional long short-term memory (LSTM) conditional random field model, a recurrent neural network model, an encoder-decoder bidirectional LSTM model, and/or the like.

The wellness system may process the text data, the audio data, the video data, the response, and the context, with one or more of the support vector machine model, the logistic regression model, or the random forest model, to determine intent data for the contextual conversation data. The intent data may include data identifying an intent associated with the conversation data (e.g., informational, authoritative, sarcastic, joking, serious, and/or the like). The wellness system may process the text data, the audio data, the video data, the response, and the context, with one or more of the conditional random field model, the bidirectional LSTM conditional random field model, or the recurrent neural network model, to determine entity data for the contextual conversation data. The entity data may include data identifying a thing, a person, a place, an object, and/or the like in the conversation data. The wellness system may process the text data, the audio data, the video data, the response, and the context, with the encoder-decoder bidirectional LSTM model, to determine dialogue act classification data for the contextual conversation data. The dialogue act classification data may include data classifying an utterance with respect to a function that the utterance serves in the contextual conversation data (e.g., an act a speaker is performing).

Figure 1F:
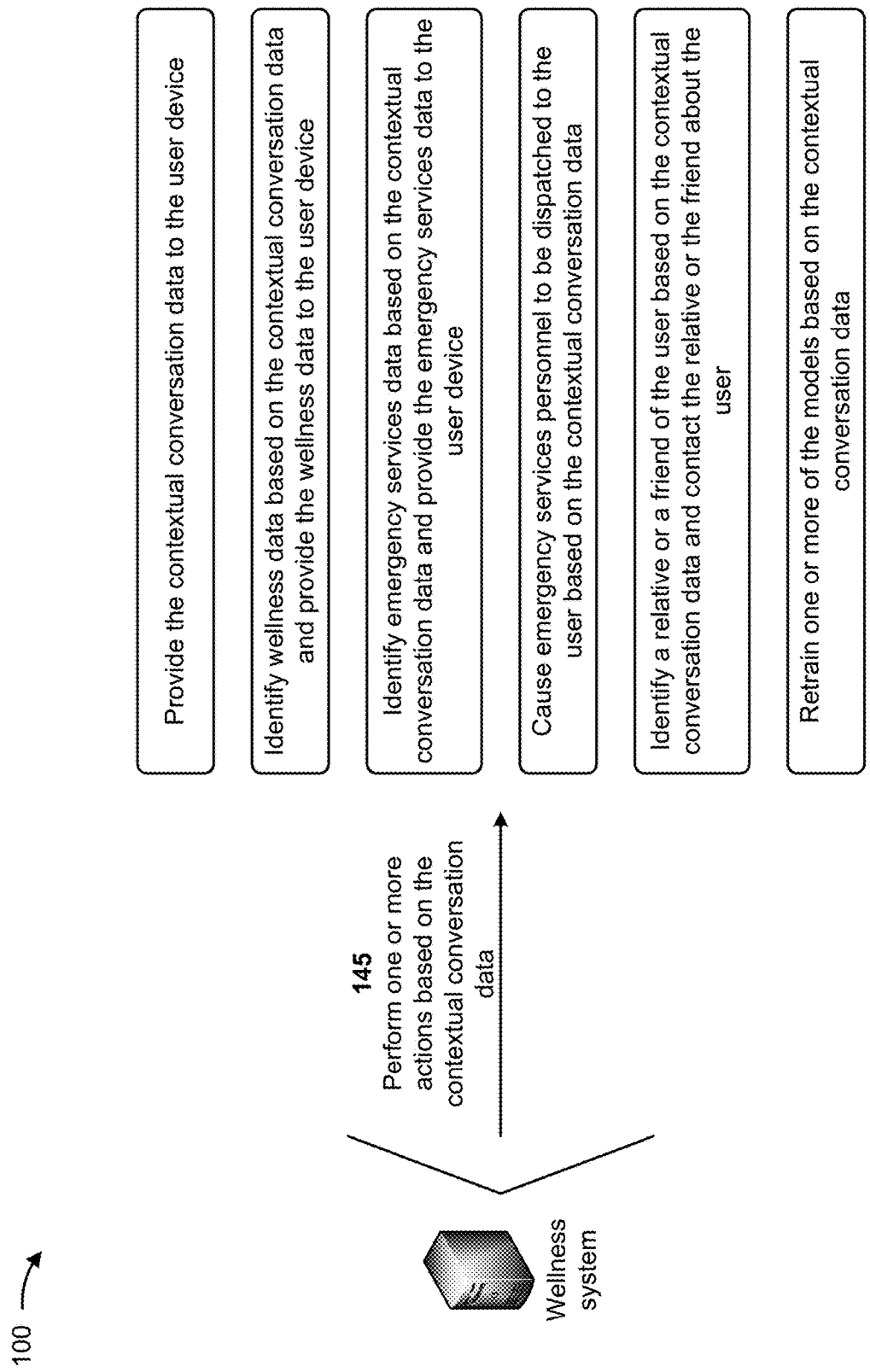

As shown in FIG. 1F, and by reference number 145, the wellness system may perform one or more actions based on the contextual conversation data. In some implementations, the one or more actions include the wellness system providing the contextual conversation data to the user device. For example, the wellness system may provide an empathetic, context-aware, and multimodal conversational agent to assist mental wellness of the user. The wellness platform may utilize the conversational agent to provide the contextual conversation data to the user device. The user of the user device may utilize the contextual conversation data to seek mental wellness help, to be reassured, to be comforted, and/or the like. In this way, the wellness system conserves computing resources, networking resources, human resources, and/or the like that would otherwise have been wasted in tracking and handling reduced work productivity of the user, tracking and handling missed workdays of the user, and/or the like.

In some implementations, the one or more actions include the wellness system identifying wellness data based on the contextual conversation data and providing the wellness data to the user device. For example, the wellness system may determine that the user suffers from anxiety based on the contextual conversation data and may identify a psychiatrist that treats anxiety. The wellness system may provide contact information for the psychiatrist to the user device so that the user may contact the psychiatrist. In this way, the wellness system conserves computing resources, networking resources, human resources, and/or the like that would otherwise have been wasted in reduced work productivity of the user due to anxiety, missed workdays of the user due to anxiety, and/or the like.

In some implementations, the one or more actions include the wellness system identifying emergency services data based on the contextual conversation data and providing the emergency services data to the user device. For example, the wellness system may determine that the user is suicidal based on the contextual conversation data, and may identify emergency services (e.g., law enforcement, a suicide hotline, and/or the like) based on the user being suicidal. The wellness system may contact the emergency services and request that help be dispatched to the user immediately, and/or the wellness system may provide contact information for the emergency services to the user device. In this way, the wellness system conserves computing resources, networking resources, human resources, and/or the like that would otherwise have been wasted in providing emergency services to the user after the user attempts to commit suicide.

In some implementations, the one or more actions include the wellness system causing emergency services personnel to be dispatched to the user based on the contextual conversation data. For example, the wellness system may contact the emergency services and request that emergency services be dispatched to the user immediately to prevent the user from attempting suicide. In this way, the wellness system conserves computing resources, networking resources, human resources, and/or the like that would otherwise have been wasted in providing emergency services to the user after the user attempts to commit suicide.

In some implementations, the one or more actions include the wellness system identifying a relative or a friend of the user based on the contextual conversation data and contacting the relative or the friend about the user. For example, the wellness system may determine that the user suffers from a mental disorder based on the contextual conversation data and may identify the relative or the friend of the user based on the user suffering from the mental disorder. The wellness system may contact the relative or the friend and request that the relative or the friend contact the user immediately and/or travel to the user (e.g., with medication for the mental disorder). In this way, the wellness system conserves computing resources, networking resources, human resources, and/or the like that would otherwise have been wasted in not helping the user with the mental disorder.

In some implementations, the one or more actions include the wellness system retraining one or more of the support vector machine model, the different regression models, the deep learning convolutional neural network model, the classifier model, the generative pretrained transformer language model, the plug and play language model, or the dialog manager models based on the contextual conversation data. The wellness system may utilize the contextual conversation data as additional training data for retraining the support vector machine model, the different regression models, the deep learning convolutional neural network model, the classifier model, the generative pretrained transformer language model, the plug and play language model, or the dialog manager models, thereby increasing the quantity of training data available for training the support vector machine model, the different regression models, the deep learning convolutional neural network model, the classifier model, the generative pretrained transformer language model, the plug and play language model, or the dialog manager models. Accordingly, the wellness system may conserve computing resources associated with identifying, obtaining, and/or generating historical data for training the support vector machine model, the different regression models, the deep learning convolutional neural network model, the classifier model, the generative pretrained transformer language model, the plug and play language model, or the dialog manager models relative to other systems for identifying, obtaining, and/or generating historical data for training machine learning models.

In some implementations, the one or more actions include the wellness system conversing with a user. For example, the wellness system may act as a friend or a companion, who tries to keep the user in good spirits, tries to guide the user to good practices (e.g., "I know yoga does wonders in such cases, don't you like to practice it?" or "instead of wasting too much time on your mobile phone playing flight games, why don't you enroll in a flying class? That would be much more enjoyable").

In this way, the wellness system utilizes machine learning models to generate automated empathetic conversations. The wellness system may ensure mental wellness in a workplace by providing empathetic advisement in a proactive, personalized, contextual, and guided manner. Employees and/or patients exposed to high stress in professional and/or personal environments may utilize the wellness system as an empathetic companion to which to talk via text, voice, and/or video. The wellness system may provide early monitoring and detection of degrees of stress and depression of users of the wellness system. The wellness system may suggest remedial measures to the users, may guide conversations to soothe the users, and may suggest appropriate counselors for the users. The wellness system provides personalized conversations, trustworthy interactions, mood-aware interactions, context-aware conversations, and/or the like. This, in turn, conserves computing resources, networking resources, human resources, and/or the like that would otherwise have been wasted in reduced work productivity, missed workdays, handling disability claims, injuries, handling grievances, handling turnover, and/or the like.

As indicated above, FIGS. 1A-1F are provided as an example. Other examples may differ from what is described with regard to FIGS. 1A-1F. The number and arrangement of devices shown in FIGS. 1A-1F are provided as an example. In practice, there may be additional devices, fewer devices, different devices, or differently arranged devices than those shown in FIGS. 1A-1F. Furthermore, two or more devices shown in FIGS. 1A-1F may be implemented within a single device, or a single device shown in FIGS. 1A-1F may be implemented as multiple, distributed devices. Additionally, or alternatively, a set of devices (e.g., one or more devices) shown in FIGS. 1A-1F may perform one or more functions described as being performed by another set of devices shown in FIGS. 1A-1F.

Figure 2:
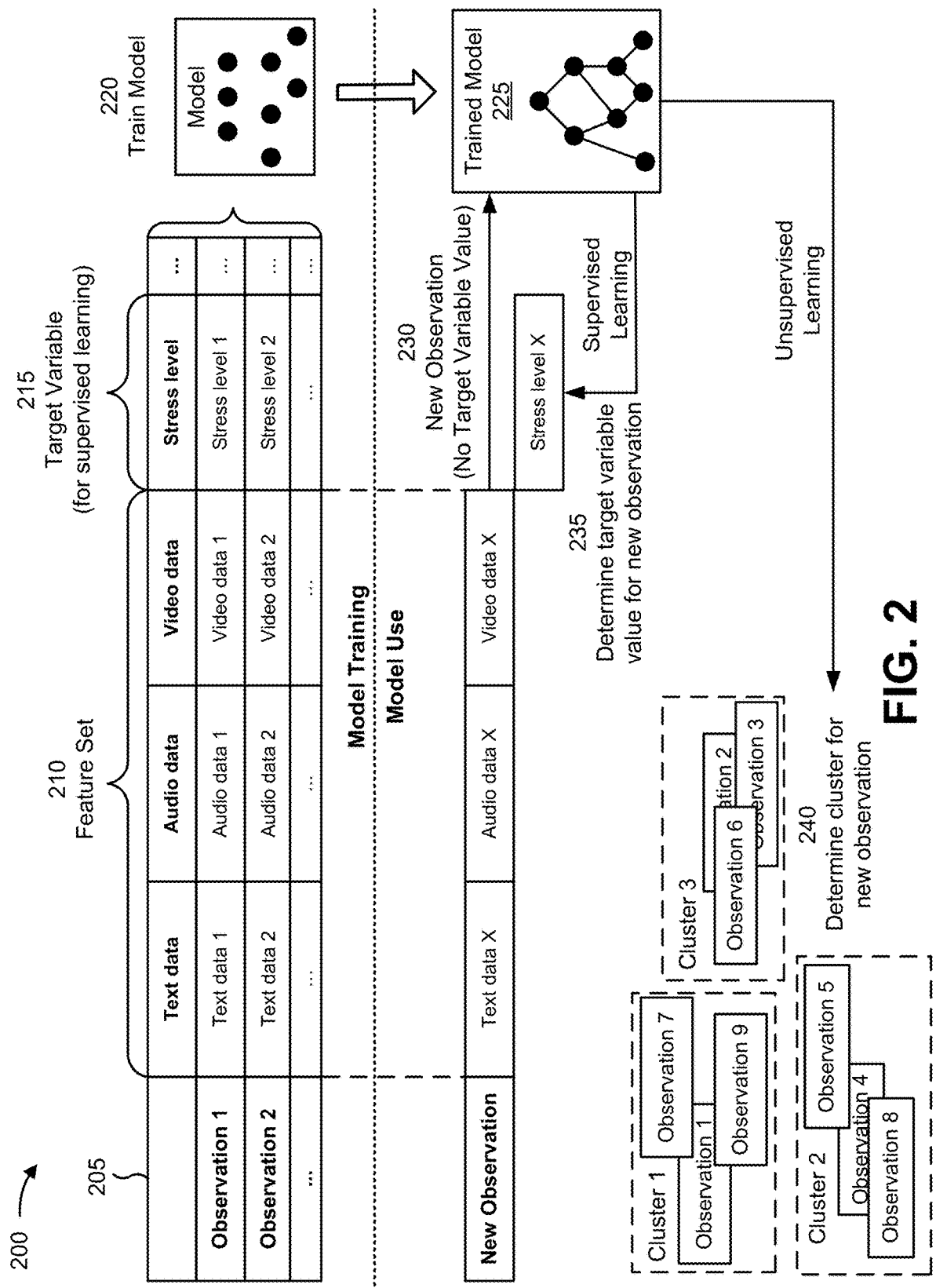
FIG. 2 is a diagram illustrating an example of training and using a machine learning model in connection with generating automated empathetic conversations.

FIG. 2 is a diagram illustrating an example 200 of training and using a machine learning model (e.g., the optimized-based poisoning model or the statistical-based poisoning model) in connection with generating automated empathetic conversations. The machine learning model training and usage described herein may be performed using a machine learning system. The machine learning system may include or may be included in a computing device, a server, a cloud computing environment, and/or the like, such as the wellness system described in more detail elsewhere herein.

As shown by reference number 205, a machine learning model may be trained using a set of observations. The set of observations may be obtained from historical data, such as data gathered during one or more processes described herein. In some implementations, the machine learning system may receive the set of observations (e.g., as input) from the wellness system, as described elsewhere herein.

As shown by reference number 210, the set of observations includes a feature set. The feature set may include a set of variables, and a variable may be referred to as a feature. A specific observation may include a set of variable values (or feature values) corresponding to the set of variables. In some implementations, the machine learning system may determine variables for a set of observations and/or variable values for a specific observation based on input received from the wellness system. For example, the machine learning system may identify a feature set (e.g., one or more features and/or feature values) by extracting the feature set from structured data, by performing natural language processing to extract the feature set from unstructured data, by receiving input from an operator, and/or the like.

As an example, a feature set for a set of observations may include a first feature of text data, a second feature of audio data, a third feature of video data, and so on. As shown, for a first observation, the first feature may have a value of text data 1, the second feature may have a value of audio data 1, the third feature may have a value of video data 1, and so on. These features and feature values are provided as examples and may differ in other examples.

As shown by reference number 215, the set of observations may be associated with a target variable. The target variable may represent a variable having a numeric value, may represent a variable having a numeric value that falls within a range of values or has some discrete possible values, may represent a variable that is selectable from one of multiple options (e.g., one of multiple classes, classifications, labels, and/or the like), may represent a variable having a Boolean value, and/or the like. A target variable may be associated with a target variable value, and a target variable value may be specific to an observation. In example 200, the target variable is a stress level, which has a value of stress level 1 for the first observation.

The target variable may represent a value that a machine learning model is being trained to predict, and the feature set may represent the variables that are input to a trained machine learning model to predict a value for the target variable. The set of observations may include target variable values so that the machine learning model can be trained to recognize patterns in the feature set that lead to a target variable value. A machine learning model that is trained to predict a target variable value may be referred to as a supervised learning model.

In some implementations, the machine learning model may be trained on a set of observations that do not include a target variable. This may be referred to as an unsupervised learning model. In this case, the machine learning model may learn patterns from the set of observations without labeling or supervision, and may provide output that indicates such patterns, such as by using clustering and/or association to identify related groups of items within the set of observations.

As shown by reference number 220, the machine learning system may train a machine learning model using the set of observations and using one or more machine learning algorithms, such as a regression algorithm, a decision tree algorithm, a neural network algorithm, a k-nearest neighbor algorithm, a support vector machine algorithm, and/or the like. After training, the machine learning system may store the machine learning model as a trained machine learning model 225 to be used to analyze new observations.

As shown by reference number 230, the machine learning system may apply the trained machine learning model 225 to a new observation, such as by receiving a new observation and inputting the new observation to the trained machine learning model 225. As shown, the new observation may include a first feature of text data X, a second feature of audio data X, a third feature of video data X, and so on, as an example. The machine learning system may apply the trained machine learning model 225 to the new observation to generate an output (e.g., a result). The type of output may depend on the type of machine learning model and/or the type of machine learning task being performed. For example, the output may include a predicted value of a target variable, such as when supervised learning is employed. Additionally, or alternatively, the output may include information that identifies a cluster to which the new observation belongs, information that indicates a degree of similarity between the new observation and one or more other observations, and/or the like, such as when unsupervised learning is employed.

As an example, the trained machine learning model 225 may predict a value of stress level X for the target variable of the stress level for the new observation, as shown by reference number 235. Based on this prediction, the machine learning system may provide a first recommendation, may provide output for determination of a first recommendation, may perform a first automated action, may cause a first automated action to be performed (e.g., by instructing another device to perform the automated action), and/or the like.

In some implementations, the trained machine learning model 225 may classify (e.g., cluster) the new observation in a cluster, as shown by reference number 240. The observations within a cluster may have a threshold degree of similarity. As an example, if the machine learning system classifies the new observation in a first cluster (e.g., a text data cluster), then the machine learning system may provide a first recommendation. Additionally, or alternatively, the machine learning system may perform a first automated action and/or may cause a first automated action to be performed (e.g., by instructing another device to perform the automated action) based on classifying the new observation in the first cluster.

As another example, if the machine learning system were to classify the new observation in a second cluster (e.g., an audio data cluster), then the machine learning system may provide a second (e.g., different) recommendation and/or may perform or cause performance of a second (e.g., different) automated action.

In some implementations, the recommendation and/or the automated action associated with the new observation may be based on a target variable value having a particular label (e.g., classification, categorization, and/or the like), may be based on whether a target variable value satisfies one or more thresholds (e.g., whether the target variable value is greater than a threshold, is less than a threshold, is equal to a threshold, falls within a range of threshold values, and/or the like), may be based on a cluster in which the new observation is classified, and/or the like.

In this way, the machine learning system may apply a rigorous and automated process to generate automated empathetic conversations. The machine learning system enables recognition and/or identification of tens, hundreds, thousands, or millions of features and/or feature values for tens, hundreds, thousands, or millions of observations, thereby increasing accuracy and consistency and reducing delay associated with generating automated empathetic conversations relative to requiring computing resources to be allocated for tens, hundreds, or thousands of operators to manually generate automated empathetic conversations.

As indicated above, FIG. 2 is provided as an example. Other examples may differ from what is described in connection with FIG. 2.

Figure 3:
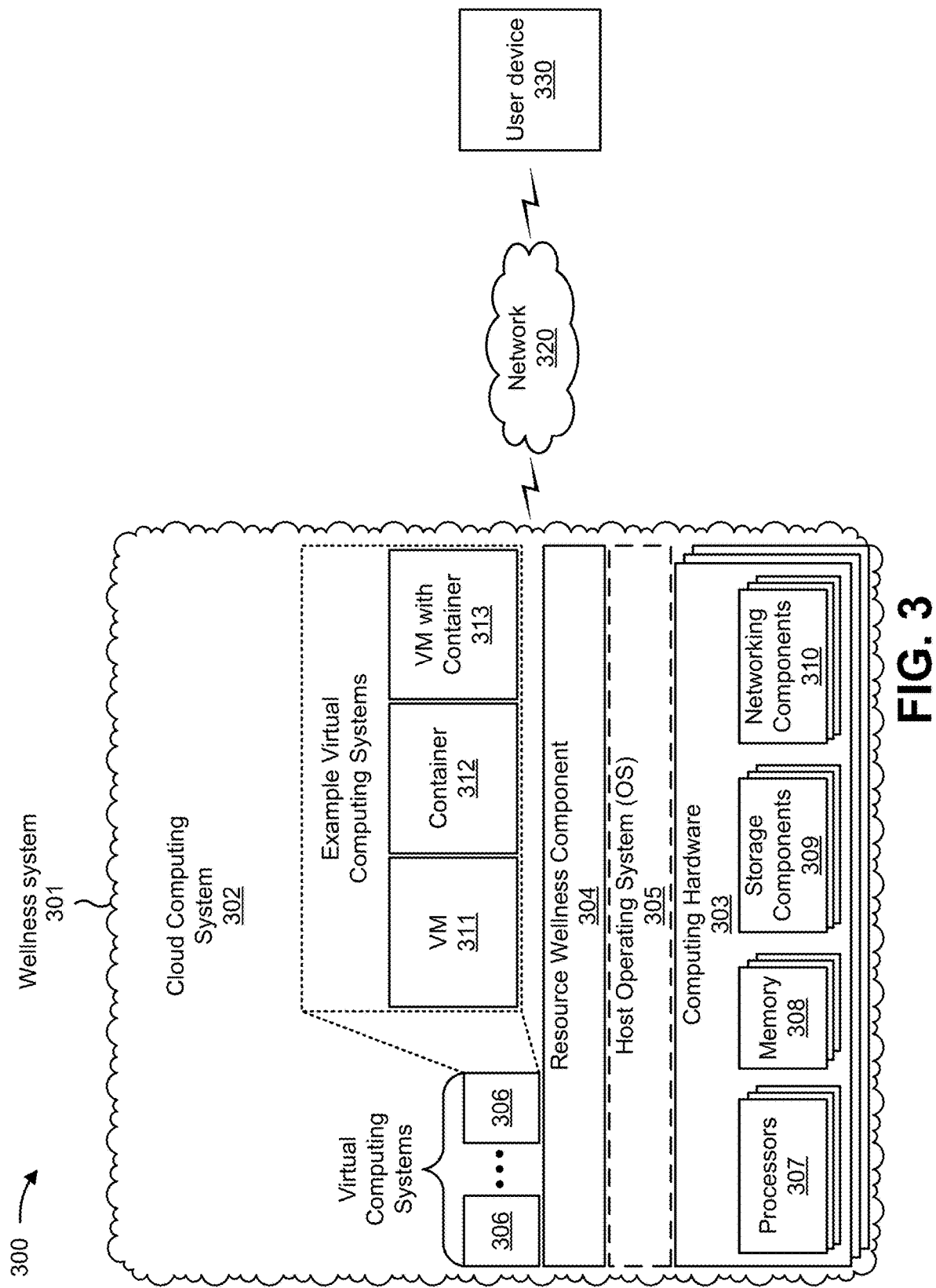
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a wellness system 301, which may include one or more elements of and/or may execute within a cloud computing system 302. The cloud computing system 302 may include one or more elements 303-313, as described in more detail below. As further shown in FIG. 3, environment 300 may include a network 320 and/or a user device 330. Devices and/or elements of environment 300 may interconnect via wired connections and/or wireless connections.

The cloud computing system 302 includes computing hardware 303, a resource management component 304, a host operating system (OS) 305, and/or one or more virtual computing systems 306. The resource management component 304 may perform virtualization (e.g., abstraction) of computing hardware 303 to create the one or more virtual computing systems 306. Using virtualization, the resource management component 304 enables a single computing device (e.g., a computer, a server, and/or the like) to operate like multiple computing devices, such as by creating multiple isolated virtual computing systems 306 from computing hardware 303 of the single computing device. In this way, computing hardware 303 can operate more efficiently, with lower power consumption, higher reliability, higher availability, higher utilization, greater flexibility, and lower cost than using separate computing devices.

Computing hardware 303 includes hardware and corresponding resources from one or more computing devices. For example, computing hardware 303 may include hardware from a single computing device (e.g., a single server) or from multiple computing devices (e.g., multiple servers), such as multiple computing devices in one or more data centers. As shown, computing hardware 303 may include one or more processors 307, one or more memories 308, one or more storage components 309, and/or one or more networking components 310. Examples of a processor, a memory, a storage component, and a networking component (e.g., a communication component) are described elsewhere herein.

The resource management component 304 includes a virtualization application (e.g., executing on hardware, such as computing hardware 303) capable of virtualizing computing hardware 303 to start, stop, and/or manage one or more virtual computing systems 306. For example, the resource management component 304 may include a hypervisor (e.g., a bare-metal or Type 1 hypervisor, a hosted or Type 2 hypervisor, and/or the like) or a virtual machine monitor, such as when the virtual computing systems 306 are virtual machines 311. Additionally, or alternatively, the resource management component 304 may include a container manager, such as when the virtual computing systems 306 are containers 312. In some implementations, the resource management component 304 executes within and/or in coordination with a host operating system 305.

A virtual computing system 306 includes a virtual environment that enables cloud-based execution of operations and/or processes described herein using computing hardware 303. As shown, a virtual computing system 306 may include a virtual machine 311, a container 312, a hybrid environment 313 that includes a virtual machine and a container, and/or the like. A virtual computing system 306 may execute one or more applications using a file system that includes binary files, software libraries, and/or other resources required to execute applications on a guest operating system (e.g., within the virtual computing system 306) or the host operating system 305.

Although the wellness system 301 may include one or more elements 303-313 of the cloud computing system 302, may execute within the cloud computing system 302, and/or may be hosted within the cloud computing system 302, in some implementations, the wellness system 301 may not be cloud-based (e.g., may be implemented outside of a cloud computing system) or may be partially cloud-based. For example, the wellness system 301 may include one or more devices that are not part of the cloud computing system 302, such as device 400 of FIG. 4, which may include a stand-alone server or another type of computing device. The wellness system 301 may perform one or more operations and/or processes described in more detail elsewhere herein.

Network 320 includes one or more wired and/or wireless networks. For example, network 320 may include a cellular network, a public land mobile network (PLMN), a local area network (LAN), a wide area network (WAN), a private network, the Internet, and/or the like, and/or a combination of these or other types of networks. The network 320 enables communication among the devices of environment 300.

User device 330 includes one or more devices capable of receiving, generating, storing, processing, and/or providing information, as described elsewhere herein. User device 330 may include a communication device and/or a computing device. For example, user device 330 may include a wireless communication device, a user equipment (UE), a mobile phone (e.g., a smart phone or a cell phone, among other examples), a laptop computer, a tablet computer, a handheld computer, a desktop computer, a gaming device, a wearable communication device (e.g., a smart wristwatch or a pair of smart eyeglasses, among other examples), an Internet of Things (IoT) device, or a similar type of device. User device 330 may communicate with one or more other devices of environment 300, as described elsewhere herein.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
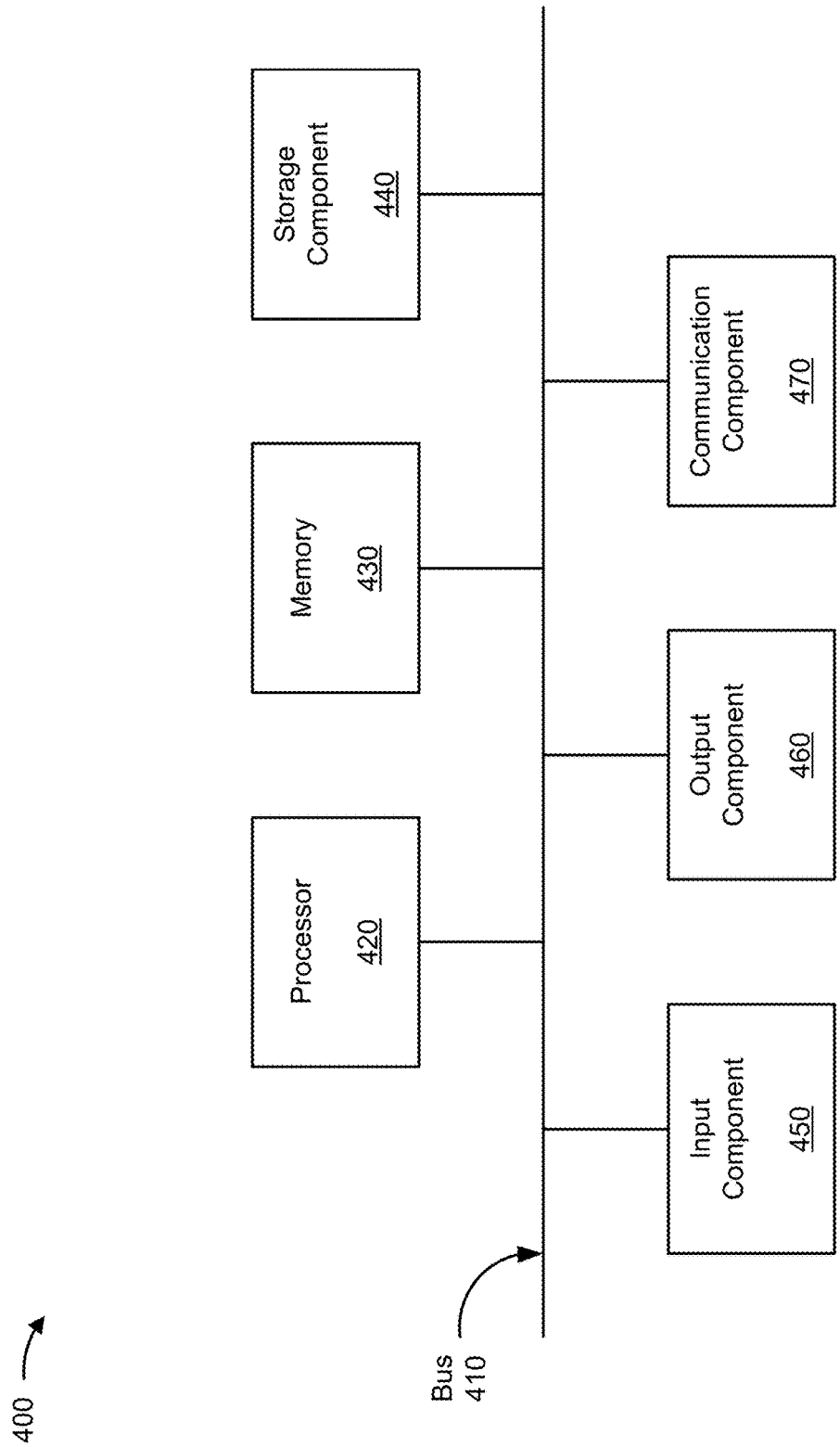
FIG. 4 is a diagram of example components of one or more devices of FIG. 3.

FIG. 4 is a diagram of example components of a device 400, which may correspond to wellness system 301 and/or user device 330. In some implementations, wellness system 301 and/or user device 330 may include one or more devices 400 and/or one or more components of device 400. As shown in FIG. 4, device 400 may include a bus 410, a processor 420, a memory 430, a storage component 440, an input component 450, an output component 460, and a communication component 470.

Bus 410 includes a component that enables wired and/or wireless communication among the components of device 400. Processor 420 includes a central processing unit, a graphics processing unit, a microprocessor, a controller, a microcontroller, a digital signal processor, a field-programmable gate array, an application-specific integrated circuit, and/or another type of processing component. Processor 420 is implemented in hardware, firmware, or a combination of hardware and software. In some implementations, processor 420 includes one or more processors capable of being programmed to perform a function. Memory 430 includes a random access memory, a read only memory, and/or another type of memory (e.g., a flash memory, a magnetic memory, and/or an optical memory).

Storage component 440 stores information and/or software related to the operation of device 400. For example, storage component 440 may include a hard disk drive, a magnetic disk drive, an optical disk drive, a solid-state disk drive, a compact disc, a digital versatile disc, and/or another type of non-transitory computer-readable medium. Input component 450 enables device 400 to receive input, such as user input and/or sensed inputs. For example, input component 450 may include a touch screen, a keyboard, a keypad, a mouse, a button, a microphone, a switch, a sensor, a global positioning system component, an accelerometer, a gyroscope, an actuator, and/or the like. Output component 460 enables device 400 to provide output, such as via a display, a speaker, and/or one or more light-emitting diodes. Communication component 470 enables device 400 to communicate with other devices, such as via a wired connection and/or a wireless connection. For example, communication component 470 may include a receiver, a transmitter, a transceiver, a modem, a network interface card, an antenna, and/or the like.

Device 400 may perform one or more processes described herein. For example, a non-transitory computer-readable medium (e.g., memory 430 and/or storage component 440) may store a set of instructions (e.g., one or more instructions, code, software code, program code, and/or the like) for execution by processor 420. Processor 420 may execute the set of instructions to perform one or more processes described herein. In some implementations, execution of the set of instructions, by one or more processors 420, causes the one or more processors 420 and/or the device 400 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 4 are provided as an example. Device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

FIG. 5 is a flowchart of an example process 500 for utilizing machine learning models to generate automated empathetic conversations. In some implementations, one or more process blocks of FIG. 5 may be performed by a device (e.g., wellness system 301). In some implementations, one or more process blocks of FIG. 5 may be performed by another device or a group of devices separate from or including the device, such as a user device (e.g., user device 330). Additionally, or alternatively, one or more process blocks of FIG. 5 may be performed by one or more components of device 400, such as processor 420, memory 430, storage component 440, input component 450, output component 460, and/or communication component 470.

As shown in FIG. 5, process 500 may include receiving, from a user device, text data identifying text input by a user of the user device, audio data identifying audio associated with the user, and video data identifying a video associated with the user (block 505). For example, the device may receive, from a user device, text data identifying text input by a user of the user device, audio data identifying audio associated with the user, and video data identifying a video associated with the user, as described above.

As further shown in FIG. 5, process 500 may include processing the text data, the audio data, and the video data, with a support vector machine model, to determine a stress level of the user (block 510). For example, the device may process the text data, the audio data, and the video data, with a support vector machine model, to determine a stress level of the user, as described above.

As further shown in FIG. 5, process 500 may include processing the text data, the audio data, and the video data, with different regression models, to determine a first depression level of the user based on the text data, a second depression level of the user based on the audio data, and a third depression level of the user based on the video data (block 515). For example, the device may process the text data, the audio data, and the video data, with different regression models, to determine a first depression level of the user based on the text data, a second depression level of the user based on the audio data, and a third depression level of the user based on the video data, as described above.

As further shown in FIG. 5, process 500 may include combining the first depression level, the second depression level, and the third depression level to identify an overall depression level of the user (block 520). For example, the device may combine the first depression level, the second depression level, and the third depression level to identify an overall depression level of the user, as described above.

As further shown in FIG. 5, process 500 may include processing the text data, the audio data, and the video data, with a deep learning convolutional neural network model, to determine a continuous affect prediction for the user (block 525). For example, the device may process the text data, the audio data, and the video data, with a deep learning convolutional neural network model, to determine a continuous affect prediction for the user, as described above.

As further shown in FIG. 5, process 500 may include processing the text data, the audio data, and the video data, with a classifier model, to determine an emotion of the user (block 530). For example, the device may process the text data, the audio data, and the video data, with a classifier model, to determine an emotion of the user, as described above.

As further shown in FIG. 5, process 500 may include processing the text data, the audio data, and the video data, with a generative pretrained transformer language model, to determine a response to the user (block 535). For example, the device may process the text data, the audio data, and the video data, with a generative pretrained transformer language model, to determine a response to the user, as described above.

As further shown in FIG. 5, process 500 may include utilizing a plug and play language model to determine a context for the response, based on the response, the stress level, the overall depression level, the continuous affect prediction, and the emotion (block 540). For example, the device may utilize a plug and play language model to determine a context for the response, based on the response, the stress level, the overall depression level, the continuous affect prediction, and the emotion, as described above.

As further shown in FIG. 5, process 500 may include utilizing one or more dialog manager models to generate contextual conversation data, based on the text data, the audio data, the video data, the response, and the context (block 545). For example, the device may utilize one or more dialog manager models to generate contextual conversation data, based on the text data, the audio data, the video data, the response, and the context, as described above.

As further shown in FIG. 5, process 500 may include performing one or more actions based on the contextual conversational data (block 550). For example, the device may perform one or more actions based on the contextual conversational data, as described above.

Process 500 may include additional implementations, such as any single implementation or any combination of implementations described below and/or in connection with one or more other processes described elsewhere herein.

In a first implementation, processing the text data, the audio data, and the video data, with the support vector machine model, to determine the stress level of the user includes determining a first stress level of the user based on the text input by the user, as provided in the text data; determining a second stress level of the user based on an intonation of a voice of the user, a rhythm of the voice, a pitch of the voice, an intensity of the voice, a loudness of the voice, and a jitter of the voice, as provided in the audio data; determining a third stress level of the user based on a head pose of the user, an eye gaze of the user, and an intensity of a facial muscle contraction of the user, as provided in the video data; and combining the first stress level, the second stress level, and the third stress level to determine the stress level of the user.

In a second implementation, alone or in combination with the first implementation, processing the text data, the audio data, and the video data, with the different regression models, to determine the first depression level of the user based on the text data, the second depression level of the user based on the audio data, and the third depression level of the user based on the video data includes processing the text data, with a first regression model, to determine the first depression level of the user; processing the audio data, with a second regression model, to determine the second depression level of the user; and processing the video data, with a third regression model, to determine the third depression level of the user.

In a third implementation, alone or in combination with one or more of the first and second implementations, combining the first depression level, the second depression level, and the third depression level to identify the overall depression level of the user includes assigning a first weight to the first depression level to generate a first weighted depression level; assigning a second weight to the second depression level to generate a second weighted depression level; assigning a third weight to the third depression level to generate a third weighted depression level; and aggregating the first weighted depression level, the second weighted depression level, and the third weighted depression level to identify the overall depression level of the user.

In a fourth implementation, alone or in combination with one or more of the first through third implementations, the continuous affect prediction for the user includes an arousal prediction for the user and a valence prediction for the user.

In a fifth implementation, alone or in combination with one or more of the first through fourth implementations, the deep learning convolutional neural network model includes a multi-modal sequence-to-sequence model.

In a sixth implementation, alone or in combination with one or more of the first through fifth implementations, the classifier model includes a random forest classifier model, and the emotion of the user includes one or more of happiness, sadness, anger, surprise, neutral, contempt, fear, or disgust.

In a seventh implementation, alone or in combination with one or more of the first through sixth implementations, the generative pretrained transformer language model includes a sentiment portion that is trained based on an emotion class and by applying a cross-entropy loss to the sentiment portion.

In an eighth implementation, alone or in combination with one or more of the first through seventh implementations, the plug and play language model includes a language model and an attribute model, and utilizing the plug and play language model to determine the context for the response includes processing the response, the stress level, the overall depression level, the continuous affect prediction, and the emotion, with the attribute model, to determine attributes and gradients; performing a forward pass with the language model to compute a likelihood of the attribute; performing a backward pass with the language model to update internal latent representations of the attribute based on the gradients; and determining the context for the response based on the updated internal latent representations of the attribute.

In an ninth implementation, alone or in combination with one or more of the first through eighth implementations, utilizing the one or more dialog manager models to generate contextual conversation data, based on the text data, the audio data, the video data, the response, and the context includes processing the text data, the audio data, the video data, the response, and the context, with one or more of another support vector machine model, a logistic regression model, or a random forest model, to determine intent data for the contextual conversation data; processing the text data, the audio data, the video data, the response, and the context, with one or more of a conditional random field model, a bidirectional long short-term memory (LSTM) conditional random field model, or a recurrent neural network model, to determine entity data for the contextual conversation data; and processing the text data, the audio data, the video data, the response, and the context, with an encoder-decoder bidirectional LSTM model, to determine dialogue act classification data for the contextual conversation data.

In a tenth implementation, alone or in combination with one or more of the first through ninth implementations, performing the one or more actions based on the contextual conversational data includes providing the contextual conversation data to the user device; identifying wellness data based on the contextual conversation data and providing the wellness data to the user device; or identifying emergency services data based on the contextual conversation data and providing the emergency services data to the user device.

In an eleventh implementation, alone or in combination with one or more of the first through tenth implementations, performing the one or more actions based on the contextual conversational data includes causing emergency services personnel to be dispatched to the user based on the contextual conversation data; identifying a relative or a friend of the user based on the contextual conversation data and contacting the relative or the friend; or retraining one or more of the support vector machine model, the different regression models, the deep learning convolutional neural network model, the classifier model, the generative pre- trained transformer language model, the plug and play language model, or the dialog manager models based on the contextual conversation data.

In a twelfth implementation, alone or in combination with one or more of the first through eleventh implementations, the context for the response includes a domain specific contextual utterance that is unscripted.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise form disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, and/or the like, depending on the context.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
receiving, by a device and from a user device, text data identifying text input by a user of the user device, audio data identifying audio associated with the user, and video data identifying a video associated with the user;
processing, by the device, the text data, the audio data, and the video data, with a support vector machine model, to determine a stress level of the user;
processing, by the device, the text data, the audio data, and the video data, with different regression models, to determine a first depression level of the user based on the text data, a second depression level of the user based on the audio data, and a third depression level of the user based on the video data;
combining, by the device, the first depression level, the second depression level, and the third depression level to identify an overall depression level of the user;
processing, by the device, the text data, the audio data, and the video data, with a deep learning convolutional neural network model, to determine a continuous affect prediction for the user;
processing, by the device, the text data, the audio data, and the video data, with a classifier model, to determine an emotion of the user;
processing, by the device, the text data, the audio data, and the video data, with a generative pretrained transformer language model, to determine a response to the user;
utilizing, by the device, a plug and play language model to determine a context for the response, based on the response, the stress level, the overall depression level, the continuous affect prediction, and the emotion;
utilizing, by the device, one or more dialog manager models to generate contextual conversation data, based on the text data, the audio data, the video data, the response, and the context; and
performing, by the device, one or more actions based on the contextual conversational data.

2. The method of claim 1, wherein processing the text data, the audio data, and the video data, with the support vector machine model, to determine the stress level of the user comprises:
determining a first stress level of the user based on the text input by the user, as provided in the text data;
determining a second stress level of the user based on an intonation of a voice of the user, a rhythm of the voice, a pitch of the voice, an intensity of the voice, a loudness of the voice, and a jitter of the voice, as provided in the audio data;
determining a third stress level of the user based on a head pose of the user, an eye gaze of the user, and an intensity of a facial muscle contraction of the user, as provided in the video data; and
combining the first stress level, the second stress level, and the third stress level to determine the stress level of the user.

3. The method of claim 1, wherein processing the text data, the audio data, and the video data, with the different regression models, to determine the first depression level of the user based on the text data, the second depression level of the user based on the audio data, and the third depression level of the user based on the video data comprises:
processing the text data, with a first regression model, to determine the first depression level of the user;
processing the audio data, with a second regression model, to determine the second depression level of the user; and
processing the video data, with a third regression model, to determine the third depression level of the user.

4. The method of claim 1, wherein combining the first depression level, the second depression level, and the third depression level to identify the overall depression level of the user comprises:
assigning a first weight to the first depression level to generate a first weighted depression level;
assigning a second weight to the second depression level to generate a second weighted depression level;
assigning a third weight to the third depression level to generate a third weighted depression level; and
aggregating the first weighted depression level, the second weighted depression level, and the third weighted depression level to identify the overall depression level of the user.

5. The method of claim 1, wherein the continuous affect prediction for the user includes an arousal prediction for the user and a valence prediction for the user.

6. The method of claim 1, wherein the deep learning convolutional neural network model includes a multi-modal sequence-to-sequence model.

7. The method of claim 1, wherein the classifier model includes a random forest classifier model, and
wherein the emotion of the user includes one or more of happiness, sadness, anger, surprise, neutral, contempt, fear, or disgust.

8. A device, comprising:
one or more memories; and
one or more processors, communicatively coupled to the one or more memories, configured to:
receive, from a user device, text data identifying text input by a user of the user device, audio data identifying audio associated with the user, and video data identifying a video associated with the user;
process the text data, the audio data, and the video data, with a support vector machine model, to determine a stress level of the user;
process the text data, the audio data, and the video data, with different regression models, to determine a first depression level of the user based on the text data, a second depression level of the user based on the audio data, and a third depression level of the user based on the video data;
assign weights to the first depression level, the second depression level, and the third depression level to generate a first weighted depression level, a second weighted depression level, and a third weighted depression level;
aggregate the first weighted depression level, the second weighted depression level, and the third weighted depression level to identify an overall depression level of the user;
process the text data, the audio data, and the video data, with a deep learning convolutional neural network model, to determine a continuous affect prediction for the user;
process the text data, the audio data, and the video data, with a classifier model, to determine an emotion of the user;
process the text data, the audio data, and the video data, with a generative pretrained transformer language model, to determine a response to the user;

utilize a plug and play language model to determine a context for the response, based on the response, the stress level, the overall depression level, the continuous affect prediction, and the emotion;

utilize one or more dialog manager models to generate contextual conversation data, based on the text data, the audio data, the video data, the response, and the context; and perform one or more actions based on the contextual conversational data.

9. The device of claim 8, wherein the generative pretrained transformer language model includes a sentiment portion that is trained based on an emotion class and by applying a cross-entropy loss to the sentiment portion.

10. The device of claim 8, wherein the plug and play language model includes a language model and an attribute model, and wherein the one or more processors, when utilizing the plug and play language model to determine the context for the response, are configured to:

process the response, the stress level, the overall depression level, the continuous affect prediction, and the emotion, with the attribute model, to determine attributes and gradients;

perform a forward pass with the language model, of the plug and play language model, to compute a likelihood of the attribute;

perform a backward pass with the language model, of the plug and play language model, to update internal latent representations of the attribute based on the gradients; and determine the context for the response based on the updated internal latent representations of the attribute.

11. The device of claim 8, wherein the one or more processors, when utilizing the one or more dialog manager models to generate contextual conversation data, based on the text data, the audio data, the video data, the response, and the context, are configured to:

process the text data, the audio data, the video data, the response, and the context, with one or more of another support vector machine model, a logistic regression model, or a random forest model, to determine intent data for the contextual conversation data;

process the text data, the audio data, the video data, the response, and the context, with one or more of a conditional random field model, a bidirectional long short-term memory (LSTM) conditional random field model, or a recurrent neural network model, to determine entity data for the contextual conversation data; and process the text data, the audio data, the video data, the response, and the context, with an encoder-decoder bidirectional LSTM model, to determine dialogue act classification data for the contextual conversation data.

12. The device of claim 8, wherein the one or more processors, when performing the one or more actions based on the contextual conversational data, are configured to one or more of:

provide the contextual conversation data to the user device;

identify wellness data based on the contextual conversation data and provide the wellness data to the user device; or identify emergency services data based on the contextual conversation data and provide the emergency services data to the user device.

13. The device of claim 8, wherein the one or more processors, when performing the one or more actions based on the contextual conversational data, are configured to one or more of:

cause emergency services personnel to be dispatched to the user based on the contextual conversation data;

identify a relative or a friend of the user based on the contextual conversation data and contact the relative or the friend; or retrain one or more of the support vector machine model, the different regression models, the deep learning convolutional neural network model, the classifier model, the generative pretrained transformer language model, the plug and play language model, or the dialog manager models based on the contextual conversation data.

14. The device of claim 8, wherein the context for the response includes a domain specific contextual utterance that is unscripted.

15. A non-transitory computer-readable medium storing a set of instructions, the set of instructions comprising:

one or more instructions that, when executed by one or more processors of a device, cause the device to:

receive, from a user device, text data identifying text input by a user of the user device, audio data identifying audio associated with the user, and video data identifying a video associated with the user;

process the text data, the audio data, and the video data, with a support vector machine model, to determine a stress level of the user;

process the text data, the audio data, and the video data, with different regression models, to determine a first depression level of the user based on the text data, a second depression level of the user based on the audio data, and a third depression level of the user based on the video data;

combine the first depression level, the second depression level, and the third depression level to identify an overall depression level of the user;

process the text data, the audio data, and the video data, with a deep learning convolutional neural network model, to determine a continuous affect prediction for the user, wherein the continuous affect prediction for the user includes an arousal prediction for the user and a valence prediction for the user;

process the text data, the audio data, and the video data, with a classifier model, to determine an emotion of the user;

process the text data, the audio data, and the video data, with a generative pretrained transformer language model, to determine a response to the user;

utilize a plug and play language model to determine a context for the response, based on the response, the stress level, the overall depression level, the continuous affect prediction, and the emotion;

utilize one or more dialog manager models to generate contextual conversation data, based on the text data, the audio data, the video data, the response, and the context; and perform one or more actions based on the contextual conversational data.

16. The non-transitory computer-readable medium of claim 15, wherein the one or more instructions, that cause the device to process the text data, the audio data, and the video data, with the support vector machine model, to determine the stress level of the user, cause the device to:

determine a first stress level of the user based on the text input by the user, as provided in the text data;

determine a second stress level of the user based on an intonation of a voice of the user, a rhythm of the voice, a pitch of the voice, an intensity of the voice, a loudness of the voice, and a jitter of the voice, as provided in the audio data;

determine a third stress level of the user based on a head pose of the user, an eye gaze of the user, and an intensity of a facial muscle contraction of the user, as provided in the video data; and combine the first stress level, the second stress level, and the third stress level to determine the stress level of the user.

17. The non-transitory computer-readable medium of claim 15, wherein the generative pretrained transformer language model includes a sentiment portion that is trained based on an emotion class and by applying a cross-entropy loss to the sentiment portion.

18. The non-transitory computer-readable medium of claim 15, wherein the one or more instructions, that cause the device to utilize the plug and play language model to determine the context for the response, cause the device to:

utilize an attribute model, of the plug and play language model, to determine an attribute and gradients based on the response, the stress level, the overall depression level, the continuous affect prediction, and the emotion;

perform a forward pass with a language model, of the plug and play language model, to compute a likelihood of the attribute;

perform a backward pass with the language model, of the plug and play language model, to update internal latent representations of the attribute based on the gradients; and determine the context for the response based on the updated internal latent representations of the attribute.

19. The non-transitory computer-readable medium of claim 15, wherein the one or more instructions, that cause the device to utilize the one or more dialog manager models to generate contextual conversation data, based on the text data, the audio data, the video data, the response, and the context, cause the device to:

process the text data, the audio data, the video data, the response, and the context, with one or more of another support vector machine model, a logistic regression model, or a random forest model, to determine intent data for the contextual conversation data;

process the text data, the audio data, the video data, the response, and the context, with one or more of a conditional random field model, a bidirectional long short-term memory (LSTM) conditional random field model, or a recurrent neural network model, to determine entity data for the contextual conversation data; and process the text data, the audio data, the video data, the response, and the context, with an encoder-decoder bidirectional LSTM model, to determine dialogue act classification data for the contextual conversation data.

20. The non-transitory computer-readable medium of claim 15, wherein the one or more instructions, that cause the device to perform the one or more actions based on the contextual conversational data, cause the device to one or more of:

provide the contextual conversation data to the user device;

identify wellness data based on the contextual conversation data and provide the wellness data to the user device;

identify emergency services data based on the contextual conversation data and provide the emergency services data to the user device;

cause emergency services personnel to be dispatched to the user based on the contextual conversation data;

identify a relative or a friend of the user based on the contextual conversation data and contact the relative or the friend; or retrain one or more of the support vector machine model, the different regression models, the deep learning convolutional neural network model, the classifier model, the generative pretrained transformer language model, the plug and play language model, or the dialog manager models based on the contextual conversation data.

* * * * *